United States Patent [19]
Cunningham et al.

[11] Patent Number: 6,071,249
[45] Date of Patent: Jun. 6, 2000

[54] METHOD AND APPARATUS FOR OBTAINING BLOOD FOR DIAGNOSTIC TESTS

[75] Inventors: David D. Cunningham, Lake Villa; Timothy P. Henning, Vernon Hills; Eric B. Shain, Glencoe; Douglas F. Young, Grayslake; Michael G. Lowery, Wildwood; Hugh W. Graham, Gurnee, all of Ill.

[73] Assignee: Abbott Laboratories, Abbott Park, Ill.

[21] Appl. No.: 08/982,324

[22] Filed: Dec. 2, 1997

Related U.S. Application Data

[63] Continuation-in-part of application No. 08/759,698, Dec. 6, 1996
[60] Provisional application No. 60/036,395, Jan. 24, 1997.

[51] Int. Cl.⁷ ...................................................... A61B 5/00
[52] U.S. Cl. ............................................ 600/578; 606/181
[58] Field of Search ................................... 600/584, 583, 600/578; 606/181

[56] References Cited

U.S. PATENT DOCUMENTS

| | | |
|---|---|---|
| 4,577,630 | 3/1986 | Nitzsche et al. . |
| 4,640,297 | 2/1987 | Bates . |
| 4,653,513 | 3/1987 | Dombrowski . |
| 5,037,431 | 8/1991 | Summers et al. . |
| 5,201,324 | 4/1993 | Swierczek . |
| 5,320,607 | 6/1994 | Ishibashi . |
| 5,368,047 | 11/1994 | Suzuki et al. ............................ 606/181 |
| 5,680,872 | 10/1997 | Sesekuro et al. ........................ 600/583 |
| 5,951,493 | 9/1999 | Douglas et al. ......................... 606/181 |

FOREIGN PATENT DOCUMENTS

| | | |
|---|---|---|
| 0021798 | 1/1981 | European Pat. Off. . |
| 0212906 | 3/1987 | European Pat. Off. . |
| 0230472 | 8/1987 | European Pat. Off. . |
| 0254203 | 1/1988 | European Pat. Off. . |
| 0371503 | 6/1990 | European Pat. Off. . |
| 0449525 | 10/1991 | European Pat. Off. . |
| 0520296 | 12/1992 | European Pat. Off. . |
| 0575952 | 12/1993 | European Pat. Off. . |
| 0671146 | 9/1995 | European Pat. Off. . |
| 0797951 | 10/1997 | European Pat. Off. . |
| 2803345 | 6/1979 | Germany . |
| 3708031 | 11/1987 | Germany . |
| 2222251 | 2/1990 | United Kingdom . |
| 9109139 | 6/1991 | WIPO . |
| 9202175 | 2/1992 | WIPO . |
| 9215863 | 9/1992 | WIPO . |
| 9303673 | 3/1993 | WIPO . |
| 9409713 | 5/1994 | WIPO . |
| 9637148 | 11/1996 | WIPO . |

*Primary Examiner*—Max Hindenburg
*Assistant Examiner*—Pamela L. Wingood
*Attorney, Agent, or Firm*—David L. Weinstein

[57] ABSTRACT

Method and apparatus for obtaining a sample of blood from a patient for subsequent diagnostic tests, e.g., glucose monitoring. In one aspect of the invention, the method comprises the steps of:
(a) forming an unobstructed opening in the area of the skin from which the sample of blood is to be extracted; and
(b) extracting the sample of blood from the unobstructed opening in the skin, with the aid of a vacuum and a stretching of the skin.

In another aspect of the invention, an apparatus for carrying out the method described previously is provided. The apparatus comprises:
(a) a device for forming an unobstructed opening in an area of skin from which said sample is to be extracted, preferably a lancing assembly; and
(b) a vacuum pump.
Preferably, the apparatus also includes a housing.

It has also been discovered that an improved design and construction of the nosepiece can provide enhanced collection of blood from the unobstructed opening in the skin. It has been discovered that by controlling the construction of the interior cavity of the nosepiece, collection of blood can be improved.

32 Claims, 16 Drawing Sheets

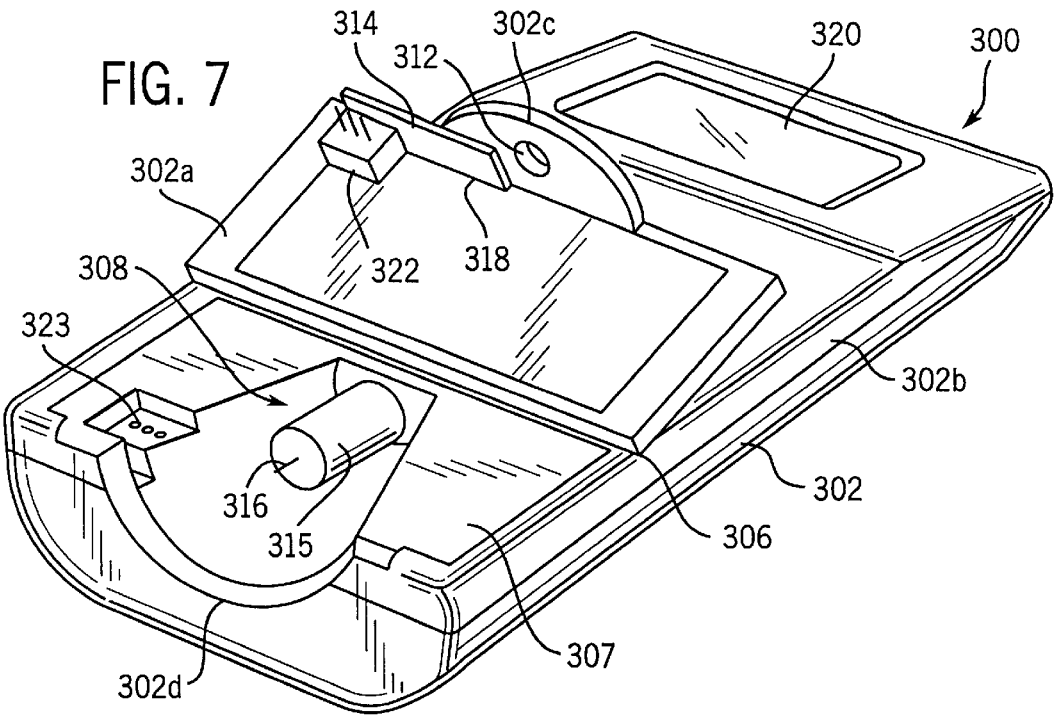

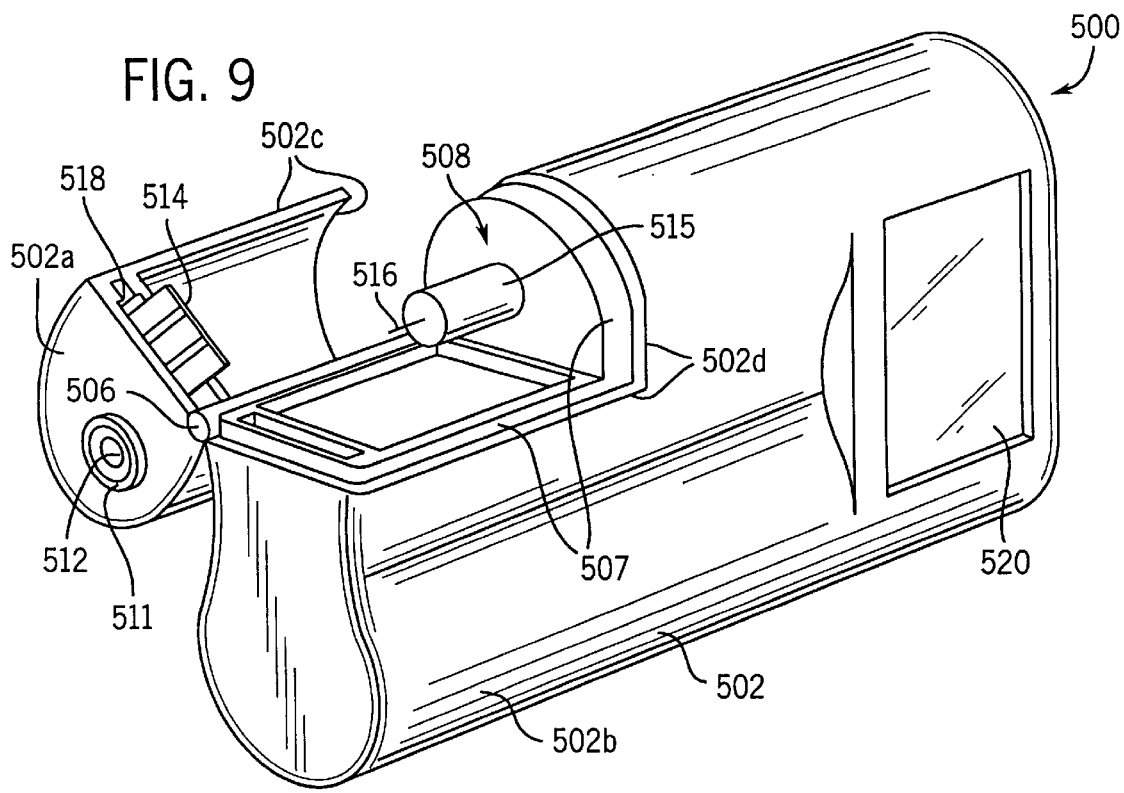
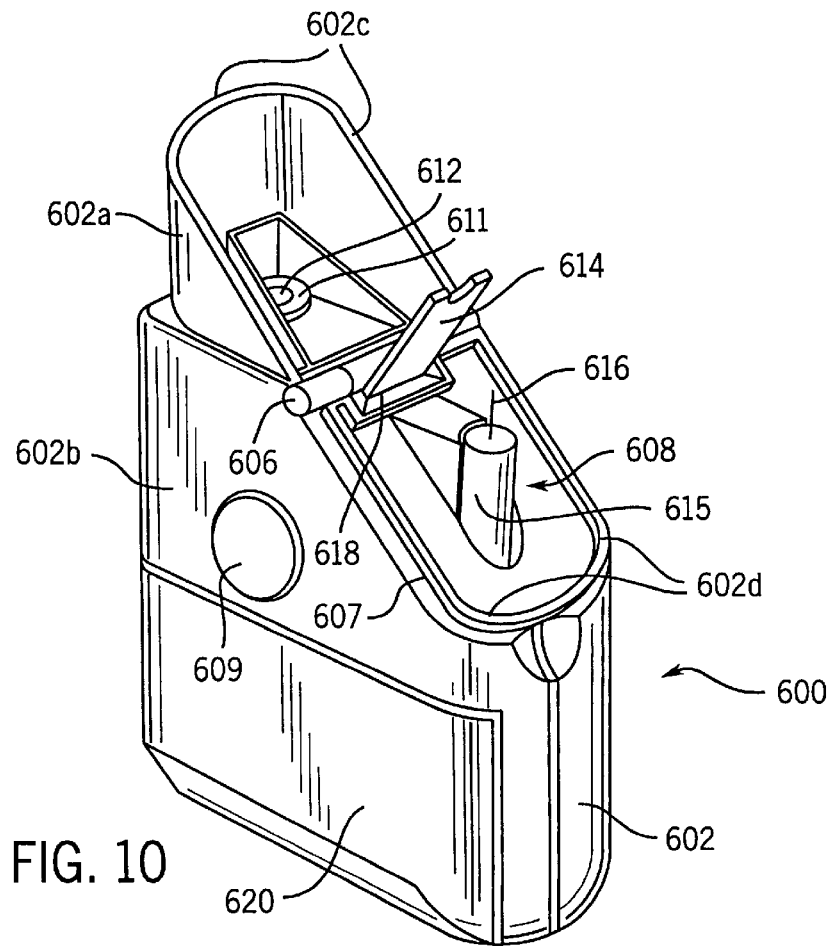

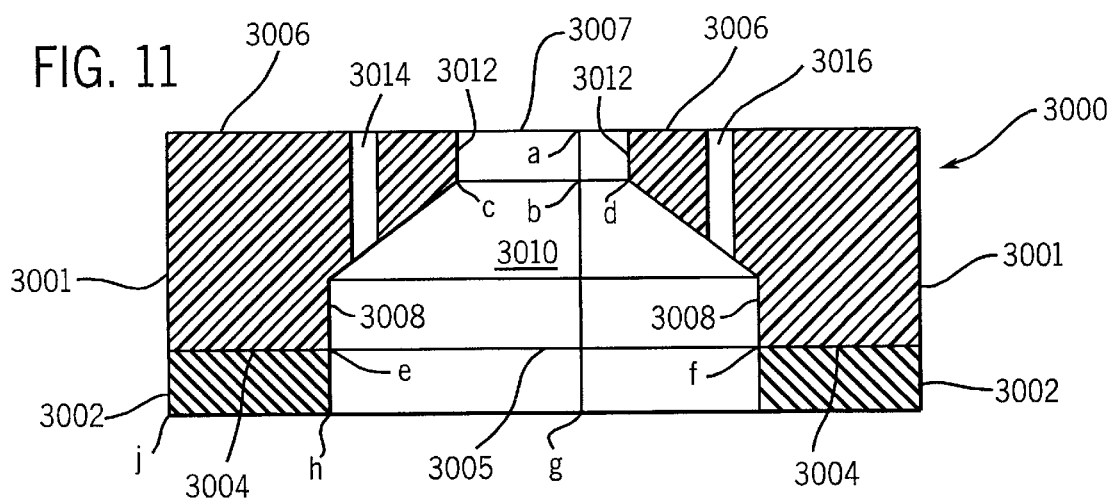
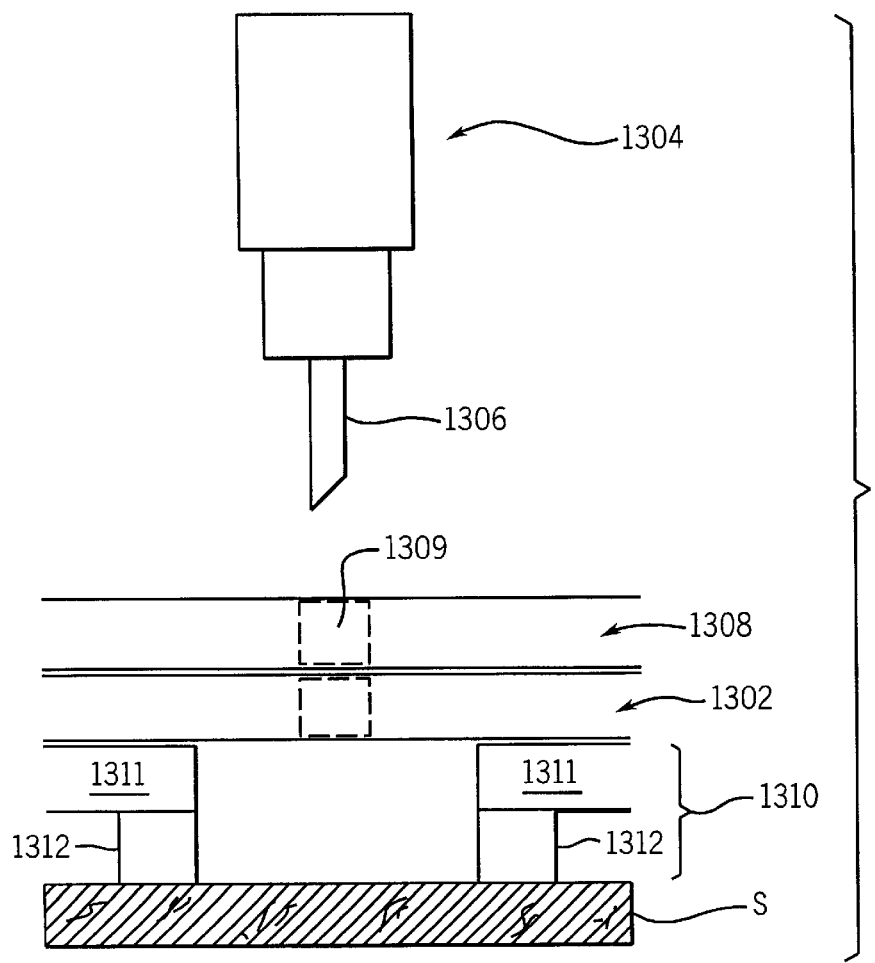

METHOD AND APPARATUS FOR OBTAINING BLOOD FOR DIAGNOSTIC TESTS

This application is a continuation-in-part of U.S. Ser. No. 08/759,698, filed Dec. 6, 1996 and a continuation-in-part of U.S. Provisional Application No. 60/036,395, filed Jan. 24, 1997.

CROSS REFERENCES TO COPENDING APPLICATIONS

This application relates to three patent applications, METHOD AND APPARATUS FOR OBTAINING BLOOD FOR DIAGNOSTIC TESTS, Attorney's Docket No. 6005.US.P1, METHOD AND APPARATUS FOR OBTAINING BLOOD FOR DIAGNOSTIC TESTS, Attorney's Docket No. 6005.US.P2, METHOD AND APPARATUS FOR OBTAINING BLOOD FOR DIAGNOSTIC TESTS, Attorney's Docket No. 6005.US.P4, filed on even-date herewith The specifications, drawings, and claims of these applications are incorporated herein by reference. All of the foregoing applications are commonly owned by the assignee of this invention.

BACKGROUND OF THE INVENTION

1. Field of the Invention

This invention relates to a method and apparatus for obtaining samples of blood for diagnostic purposes.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

The medical apparatus of the prior art for monitoring the level of glucose in the blood stream required that an individual have separately available a needle or lancet for extracting blood from the individual, strips carrying blood chemistry for creating a chemical reaction with respect to the glucose in the blood stream and changing color, and a blood glucose meter for reading the change in color indicating the level of glucose in the blood stream. The level of blood glucose, when measured by a glucose meter, is read from a strip carrying the blood chemistry through the well-known process of reading reflectometers for glucose oxidation.

Generally lancets comprise a blade and a pressable end opposed thereto, with the blade having an acute end capable of being thrust into skin of a human. By striking the pressable portion, the acute end of the blade will pierce the skin, for example, of the finger. The finger lancet is primarily used to obtain small volumes of blood, i.e., less than 1 mL. Diabetics use the finger lancet to obtain volumes of blood less than 25 $\mu$L for analysis for glucose. A small amount of blood for the blood test will ooze out of the skin. There are many small blood vessels in each finger so that a finger can be squeezed to cause a larger drop of blood to ooze. The finger is one of the most sensitive parts of the body; accordingly, the finger lancet leads to even more pain than what would be experienced by extracting blood via lancet at a different body site. The finger lancet presents another problem because of the limited area available on the fingers for lancing. Because it is recommended that diabetics monitor their blood glucose levels four to six times per day, the limited area on the fingers calls for repeated lancing of areas that are already sore. Because fingers are sensitive to pain, it is a recent tendency that the arm is subjected to blood sampling. See, for example, U.S. Pat. No. 4,653,513. The device of U.S. Pat. No. 4,653,513 comprises a cylindrical housing and a lancet support, which has a gasket or flexible portion slidably accommodated in the housing. Springs will retract the lancet support to thereby reduce air pressure in the housing so that it sucks a blood sample, automatically and immediately after a lancet pierces the skin. See also U.S. Pat. No. 5,320,607, which discloses a device comprising a sealed vacuum chamber in a state of preexisting reduced pressure, a support member for the sealed vacuum chamber, the support member defining a suction portion adjacent the sealed vacuum chamber, the suction portion, in cooperation with the sealed vacuum chamber, exposing an area of the skin of a patient to a reduced pressure state when the device is actuated, and means arranged within the suction portion for slightly rupturing a portion of the area of skin of the patient exposed to the reduced pressure state.

Because the blood volume requirements for a standard glucose test strip is typically 3 $\mu$L or more, an area of the body that can generate that much blood from a lancet wound must be used. It is believed, however, that improvements in glucose test strip technology will reduce the volume of blood needed to 1 to 3 $\mu$L. Because the finger is well supplied with blood and the amount of blood can be increased by squeezing the finger after lancing, the finger is the currently preferred body site for lancing, even though lancing of the finger is painful.

A less painful technique for obtaining body fluids could be found if a reliable method were found for lancing a body part that is less sensitive to pain than the finger and obtaining a useful amount of blood from that body part. A body part such as the forearm is much less sensitive to pain than the finger, but the amount of blood resulting from the lancing procedure is generally of an inadequate volume for use with current detection technology. Ways of increasing blood flow to the finger are common knowledge. The recommendation is made to diabetics to run their finger under hot water prior to lancing to improve the blood flow in the finger and the amount of blood collected from the finger. Running hot water over a body part to improve blood flow is impractical for areas such as the forearm or thigh. The availability of hot water is also a concern.

It would be desirable to develop a technique and apparatus for obtaining blood for diagnostic purposes in a painless, reliable manner.

SUMMARY OF THE INVENTION

This invention provides a method and apparatus for extracting a sample of blood from a patient for subsequent diagnostic tests, e.g., glucose monitoring. In one aspect of the invention, the method comprises the steps of:

(a) forming an unobstructed opening in the area of the skin from which the sample of blood is to be extracted; and (b) extracting the sample of blood from the unobstructed opening in the skin, with the aid of vacuum and stretching of the skin.

In a preferred embodiment of the method, step (a) is preceded by the step of increasing the availability of blood in the portion of the skin from which the sample is to be extracted. In this preferred embodiment, the availability of blood in the portion of the skin from which the sample is to be extracted can be increased by means of a vacuum, which is applied to the surface of the skin in the vicinity of the opening prior to forming the opening in the skin. The vacuum causes the portion of the skin in the vicinity of the blood extraction site to become engorged with blood. The vacuum also causes the portion of the skin in the vicinity of the blood extraction site to become stretched. An opening in this stretched portion of skin can be formed with a cutting or puncturing device, e.g., a lancet, or other device capable of forming an opening in the skin, e.g., a laser or a fluid jet. If a cutting or puncturing device is used to form the opening, it must be retracted from the opening prior to the step of extracting the sample of blood from the opening. This retraction will allow the unrestricted flow of blood through the opening. After the opening is formed, a vacuum is used to aid in extracting the sample of blood from the opening in the skin. The sample can be analyzed from the drops of blood that collect on the surface of the skin at the site of the opening by applying the blood directly to a glucose detector. It is preferred, however, that the sample be collected in such a manner, e.g., via a capillary tube, that it can be analyzed by conventional diagnostic devices, such as, for example, a biosensor. In another preferred embodiment, the sample can be collected in a collection zone that is integrated with a conventional diagnostic device, e.g., a biosensor.

In an alternative of the aforementioned preferred embodiment, the availability of blood in the area of the skin from which the sample is to be extracted can be increased by means of applying thermal energy to that area of skin. The thermal energy causes the blood in that area of the skin to flow more rapidly, thereby allowing more blood to be collected per given unit of time. In this alternative embodiment, steps (a) and (b) can be carried out in the same manner as they were carried out in the aforementioned preferred embodiment.

In another aspect of the invention, an apparatus for collecting a sample of body fluid for analysis in a diagnostic test, e.g., blood, is provided. In a preferred embodiment, the apparatus comprises:

(a) a housing;
(b) a device for forming an unobstructed opening in an area of skin from which said sample is to be extracted, preferably a lancing assembly; and
(c) a vacuum pump.

It is also possible to dispense with the housing. However, the housing is preferred for the convenience of the patient and the protection of the components.

The vacuum pump requires a source of power. If the apparatus includes a housing, the source of power can be disposed within the housing. Alternatively, the source of power can be external to the housing.

The preferred device for forming an unobstructed opening in the area of the skin from which the sample of blood is to be extracted is a lancing assembly, which comprises a lancet for forming an opening in the skin. Alternatively, the unobstructed opening in the skin can be formed by a laser or a fluid jet.

The vacuum pump can serve the dual purposes of (1) stretching the skin and (2) enhancing the extraction of the sample of blood from the unobstructed opening in the skin. Preferably, the vacuum pump can serve the triple purposes of (1) stretching the skin, (2) increasing the availability of blood to the area of the skin from which the sample is to be extracted, and (3) enhancing the extraction of the sample of blood from the unobstructed opening in the skin. Preferably, the housing further contains electronics having programmed instructions to switch the vacuum pump on and off to maintain the desired level of vacuum.

The apparatus preferably contains valves, such as, for example, solenoid valves, for triggering the lancet of the lancing assembly and releasing the vacuum at the conclusion of the blood extraction procedure. The apparatus can optionally contain a heating element to increase the availability of blood to the area of the skin from which the sample is to be extracted. The apparatus can also contain a glucose detector integrated with the apparatus, e.g., a biosensor, to analyze the sample of blood collected by the apparatus.

The method and apparatus of this invention provide several advantages over the methods and apparatus of the prior art. First, a sufficient amount of blood can be extracted from parts of the body, other than the finger, for conducting glucose monitoring tests. Second, by rendering other parts of the body suitable for extracting blood, the use of a painful finger lance can be avoided. Third, by increasing the availability of blood at the site where the blood is to be extracted, the period of time required for extracting the sample can be reduced. Because of these advantages, the diabetic patient is more likely to monitor glucose levels in the blood at the intervals prescribed by his doctor.

BRIEF DESCRIPTION OF THE DRAWINGS

FIG. 2 also illustrates the spatial relationship between the nosepiece of lancing assembly and a glucose detector, e.g., a biosensor.

FIG. 7 is a perspective view of an embodiment of the apparatus of this invention. In this figure, the housing of the apparatus is open.

FIG. 8 is a perspective view of an embodiment of the apparatus of this invention. In this figure, the housing of the apparatus is open.

FIG. 9 is a perspective view of an embodiment of the apparatus of this invention. In this figure, the housing of the apparatus is open.

FIG. 10 is a perspective view of an embodiment of the apparatus of this invention. In this figure, the housing of the apparatus is open.

FIG. 11 is an elevational view of a cross section of a preferred embodiment of a nosepiece of this invention.

FIGS. 13A, 13B, 13C, and 13D are schematic diagrams of the positioning of the nosepiece of the apparatus of this invention relative to the lancing assembly, the detection element, and the skin prior to application of vacuum, during application of vacuum, during lancing, and during blood collection and analysis, respectively.

DETAILED DESCRIPTION

Figure 1:
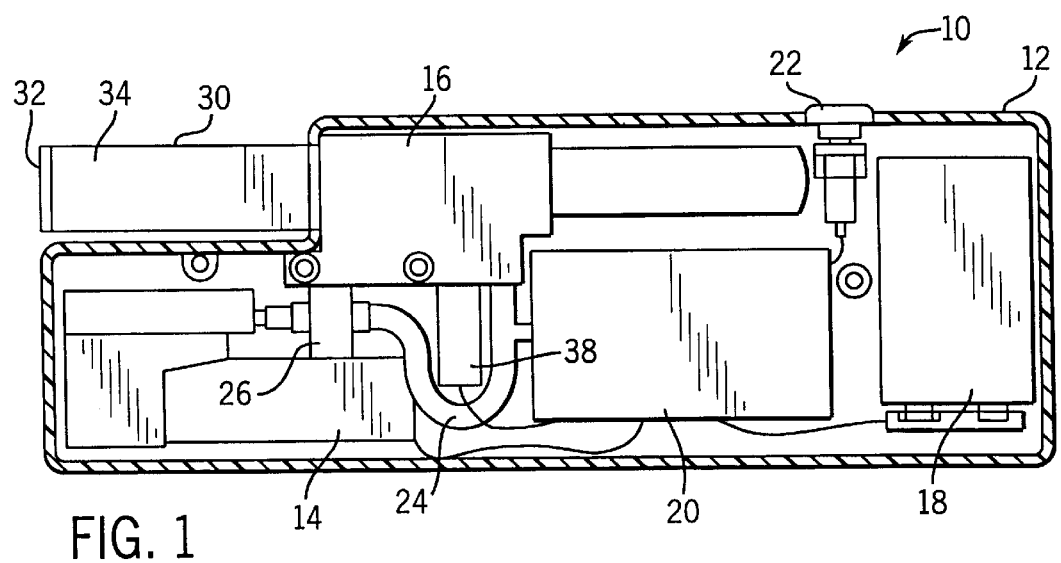
FIG. 1 is a plan view of the components of a preferred embodiment of the apparatus of this invention. In this Figure, the cover of the housing is removed.

The embodiments of this invention require the following steps to carry out the function of obtaining a sample of blood for carrying out a diagnostic test, e.g., glucose monitoring:

(a) forming an unobstructed opening in the area of the skin from which the sample of blood is to be extracted; and (b) extracting the sample of blood from the unobstructed opening in the skin, with the aid of a vacuum and a stretching of the skin.

The step of forming an unobstructed opening in the area of the skin from which the sample of blood is to be extracted is carried out by a piercing device or some other type of device capable of forming an unobstructed opening in the skin. Piercing devices suitable for this invention include, but are not limited to, mechanical lancing assemblies. Other type of device capable of forming an unobstructed opening in the skin include, but are not limited to, lasers and fluid jets. Other types of devices capable of forming an unobstructed opening in the skin can be used, and this disclosure should not be construed so as to be limited to the devices listed. Mechanical lancing assemblies are well-known in the art. These assemblies comprise include standard steel lancets, serrated devices, and multiple tip devices. The lancets can be made from metal or plastic. Multiple tip devices provide redundancy, which can reduce the number of failures and increase the volume of blood extracted.

Lasers suitable for forming an unobstructed opening in the skin to draw blood are also well-known in the art. See for example, U.S. Pat. Nos. 4,775,361, 5,165,418, 5,374,556, International Publication Number WO 94/09713, and Lane et al. (1984) IBM Research Report—"Ultraviolet-Laser Ablation of Skin", all of which are incorporated herein by reference. Lasers that are suitable for forming an unobstructed opening in the skin the skin include Er:YAG, Nd:YAG, and semiconductor lasers.

Fluid jets suitable for forming an unobstructed opening in the skin employ a high pressure jet of fluid, preferably a saline solution, to penetrate the skin.

Regardless of what type of device is utilized to form an unobstructed opening in the skin, the opening formed by the device must be unobstructed. As used herein, the term "unobstructed" means free from clogging, hampering, blocking, or closing up by an obstacle. More specifically, the expressions "unobstructed opening in the area of the skin from which the sample is to be extracted", "unobstructed opening in the skin", and the like are intended to mean that the portion of the opening below the surface of the skin is free from any foreign object that would clog, hamper, block, or close up the opening, such as, for example, a needle of any type. For example, if a lancet is used to form the opening, it must be retracted from the opening prior to the commencement of the extraction of blood. Because lasers and fluid jets do not require contact with the skin to form openings in the skin, these types of devices typically provide unobstructed openings. However, these expressions are rot intended to include foreign objects at the surface of the skin or above the surface of the skin, such as, for example, a glucose monitor. This feature, i.e., the unobstructed opening, can be contrasted with the opening used in the method and apparatus described in U.S. Pat. No. 5,320,607, in which the piercing and cutting means remains in the skin during the duration of the period of blood extraction. By leaving the opening unobstructed, blood can be extracted much more rapidly from the opening than it would be extracted if the piercing and cutting means were allowed to remain in the opening. In addition, the requirement of an unobstructed opening exposes the body to a foreign object either not at all or for only a very short period of time, which is welcomed by the patient.

The step of extracting the sample of blood from the opening in the skin is carried out by a combination of extraction enhancing elements. Extraction enhancing elements suitable for use in this invention include, but are not limited to, vacuum, skin stretching elements, and heating elements. It has seen discovered that when these elements are used in combination, the volume of blood extracted is greatly increased, particularly when a vacuum is applied in combination with skin stretching. In this combination, the vacuum not only causes the blood to be rapidly removed from the unobstructed opening by suction, it also causes a portion of the skin in the vicinity of the opening to be stretched. Stretching of the skin can be effected by other means, such as mechanical means or adhesives. Mechanical means include devices for pinching or pulling the skin; adhesives bring about stretching of the skin by means of pulling. It is preferred to use a vacuum to effect stretching of the skin. Like a vacuum, a heating element operates more effectively in combination with other techniques, e.g., stretching of the skin.

In the preferred embodiment of this invention, step (a), the step of forming the unobstructed opening, is preceded by the step of increasing the availability of blood at the area of the skin from which the sample is to be extracted. The availability of blood at a given area of the skin can be increased by at least two methods. In one method, a vacuum can be used to cause blood flowing through blood vessels to pool in the area of the skin where the vacuum is applied. In another method, heat can be used to cause blood flowing through blood vessels to flow more rapidly in the area of the skin where heat is applied, thereby allowing a greater quantity of blood to be extracted from the blood extraction site per unit of time. Although the step of increasing the availability of blood in the vicinity of the blood extraction site is not required, the employment of this step can result in a greater volume of blood extracted. Elements for increasing the availability of blood at a blood extraction site that are suitable for use in this invention include, but are not limited to, vacuum, localized heating element, skin stretching element, and chemicals. As stated previously, applying a vacuum to the area of the skin from which blood is to be extracted can increase blood availability under and within the skin at the application site. The vacuum can also be used to stretch the skin upwardly into a chamber, thereby increasing pooling of blood under and within the skin. This combination of vacuum and skin stretching can be an extension of the combination used to extract blood from the opening in the skin, as previously described. It is well-known that heat can increase perfusion on the large scale of a limb or a finger. Chemical means, such as histamine, can be used to cause a physiological response to increase perfusion under and within the skin.

In the preferred embodiments of the invention, the extracted blood is also collected. The step of collecting the sample of blood can be carried out in a variety of ways. For example, the blood can be collected in capillary tubes or absorbent paper. Alternatively, the blood can be allowed to remain in the lancet assembly, from which it can used directly in a diagnostic test. Most preferably, the sample of blood is collected on the application zone of a glucose detector, from where it can be used directly to provide an indication of the concentration of glucose in the blood. Regardless of the manner in which the blood sample is collected, the sample can be analyzed at a time later than the time of collection or at a location remote from the location of collection or both.

A preferred embodiment of the invention will now be described in detail. Blood extraction device 10 comprises a housing 12. Disposed within the housing 12 are a vacuum pump 14, a lancing assembly 16, a battery 18, and electronics 20. A switch 22 is provided to activate electronics 20.

The housing 12 is preferably made from a plastic material. It is preferably of sufficient size to contain all of the components that are required for forming an unobstructed opening in the area of the skin from which the sample of blood is to be extracted, extracting the sample of blood from the unobstructed opening in the skin, preferably with the aid of a vacuum and a stretching of the skin, and collecting the extracted sample in an amount sufficient to carry out a diagnostic test. Methods of preparing the housing 12 are well-known to one of ordinary skill in the art. As stated previously, the housing 12 is not required, but is preferred for the convenience of the patient and the protection of the components.

The vacuum pump 14 must be capable of providing a vacuum that will provide sufficient suction to stretch the portion of the skin in the region from which the sample of blood is to be extracted. Typically, the portion of stretched skin is raised a distance of 1 to 10 mm, preferably 3 to 5 mm, from the plane of the body part of which it is a portion. As the suction provided by the vacuum pump 14 is stretching the appropriate portion of skin, the suction provided by the vacuum pump 14 also causes the stretched portion to become engorged with blood. The level of suction provided must be sufficient to cause a relatively large volume of blood to become engorged at the point that the vacuum is applied. The vacuum pump 14 must also be capable of providing sufficient suction to extract blood from the opening in the skin at a rate sufficient to extract at least 1 $\mu$L of blood within a period of five minutes. A vacuum pump 14 that is suitable for the device of this invention can be a diaphragm pump, a piston pump, a rotary vane pump, or any other pump that will perform the required functions set forth previously. Typically, the vacuum pump 14 employs a self-contained permanent magnet DC motor. Vacuum pumps that are suitable for this invention are well-known to those of ordinary skill in the art and are commercially available. A vacuum pump suitable for use in the present invention is available from T-Squared Manufacturing Company, Nutley, N.J., and has the part number T2-03.08.004.

The vacuum pump 14 is preferably capable of providing a pressure of down to about −14.7 psig, and is more preferably operated at from about −3.0 psig to about −10.0 psig. The area of the skin subjected to vacuum preferably ranges up to about 50 $cm^2$, more preferably from about 0.1 to about 5.0 $cm^2$. The period of vacuum application prior to forming the opening in the skin, i.e., for increasing the availability of blood to the application site, preferably ranges up to about 5 minutes, preferably from about 1 to about 15 seconds. The period of vacuum application subsequent to forming the opening in the skin, i.e., for aiding in the extraction of blood from the unobstructed opening, preferably ranges up to about 5 minutes, preferably from about 1 to about 60 seconds. The vacuum provided by the vacuum pump 14 can be continuous or pulsed. A continuous vacuum is preferred for the reason that it requires fewer components than does a pulsed vacuum. It is preferred that the vacuum applied not cause irreversible damage to the skin. It is preferred that the vacuum applied not produce bruises and discolorations of the skin that persist for several days. It is also preferred that the level of vacuum applied and duration of application of vacuum not be so excessive that it causes the dermis to separate from the epidermis, which results in the formation of a blister filled with fluid.

The vacuum pump feature offers significant advantages over the method and apparatus described in U.S. Pat. No. 5,320,607, in which a sealed vacuum chamber in a state of preexisting reduced pressure is used. The use of a vacuum pump provides the user with greater control of blood extraction conditions than does a sealed vacuum chamber in a state of preexisting reduced pressure. For example, if the vacuum is insufficient, energy can be provided to the vacuum pump to bring about a higher level of vacuum, thereby providing greater suction.

The lancing assembly 16 comprises at least one lancet. Standard lancets can be used in the lancing assembly of this invention. Narrow gauge (28 to 30 gauge) lancets are preferred. Lancets suitable for this invention can be made from metal or plastic. Lancets suitable for this invention can have single points or multiple points. The depth of penetration of the lancet preferably ranges from about 0.4 to about 2.5 mm, more preferably from about −0.4 to about 1.6 mm. The length of the lancet or lancets preferably ranges from about 1 mm to about 5 mm. The lancing assembly is preferably located so that the user can easily replace used lancets. The lancet of the lancing assembly 16 can be cocked manually or automatically, e.g., by means of a vacuum-actuated piston or diaphragm. The lancet of the lancing assembly 16 can be triggered by manually or automatically, e.g., by means of a vacuum-actuated piston or diaphragm.

Lancing assemblies are well-known in the art. Representative examples of lancing assemblies suitable for this invention are described in U.S. Pat. Nos. Re. 32,922, 4,203, 446, 4,990,154, and 5,487,748, all of which are incorporated herein by reference. A particularly suitable lancing assembly for this invention is described in U.S. Pat. No. Re. 32,922. However, any lancing assembly selected should operate in conjunction with the other features of the apparatus of this invention. For example, if a vacuum is employed, the lancing assembly must be designed so that a vacuum can be formed and drawn through the assembly. The lancing assembly can be designed to allow automatic cocking and automatic triggering of the lancet.

The vacuum pump 14 is connected to the lancing assembly 16 by an evacuation tube 24. The air that is evacuated from the lancing assembly 16 by the vacuum pump 14 is removed via the evacuation tube 24. The evacuation tube 24 is typically made from a polymeric material. A check valve 20 is placed between the vacuum pump 14 and the lancing assembly 16 at a point in the evacuation tube 24 to prevent air removed from the lancing assembly 16 by the vacuum pump 14 from flowing back to the lancing assembly 16 and adversely affecting the vacuum.

A source of power for the vacuum pump 14 can be disposed within the housing 12. A source of power suitable for the device of this invention is a battery 18. Alternatively, an external source of power can be used to operate the vacuum pump 14. The power source is actuated by the electronics 20, which, in turn, is actuated by the switch 22.

The electronics 20 may incorporate a microprocessor or microcontroller. The function of the electronics 20 is to switch power on and off to operate the various components in the apparatus. These components include, but are not limited to, the vacuum pump 14. The electronics 20 can also be use to switch power on and off to operate components in alternative embodiments, e.g., heating elements, lancets, indicating devices, and valves. Electronics suitable for this invention is the "TATTLETALE MODEL 5F" controller/data logger, commercially available from Onset Computer Corporation, 536 MacArthur Blvd. P.O. Box 3450, Pocasset, Mass. 02559-3450. Auxiliary electronic devices, such as power transistors, pressure monitors, and OP-Amps (operational amplifiers), may also be required in order to provide an interface between the controller and the operational components. All electronics required for this invention are well-known to one of ordinary skill in the art and are commercially available. Auxiliary electronic devices suitable for use in this invention include the following components:

| Component | Source | Catalog Number |
| --- | --- | --- |
| Mosfet Drivers | International Rectifier El Segundo, CA | IRLD024 |
| Op-Amp | National Semiconductor Santa Clara, CA | LM358 |
| Status LED | Hewlett-Packard Newark Electronics Schaumburg, IL | HLMPD150 |
| Pressure Sensor | Sensym, Inc. Milpitas, CA | SDX15D4 |

Figure 3:
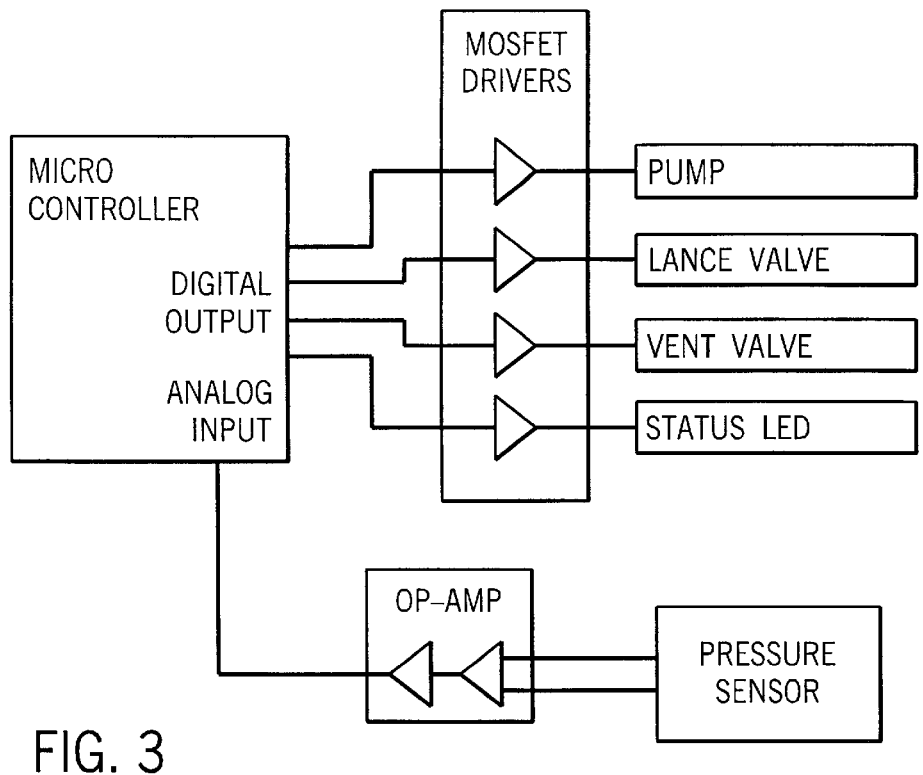
FIG. 3 is a block diagram illustrating the electronics of the preferred embodiment.

FIG. 3 illustrates by way of a block diagram how the foregoing electronic components can be arranged to carry out the method of the present invention.

Figure 2:
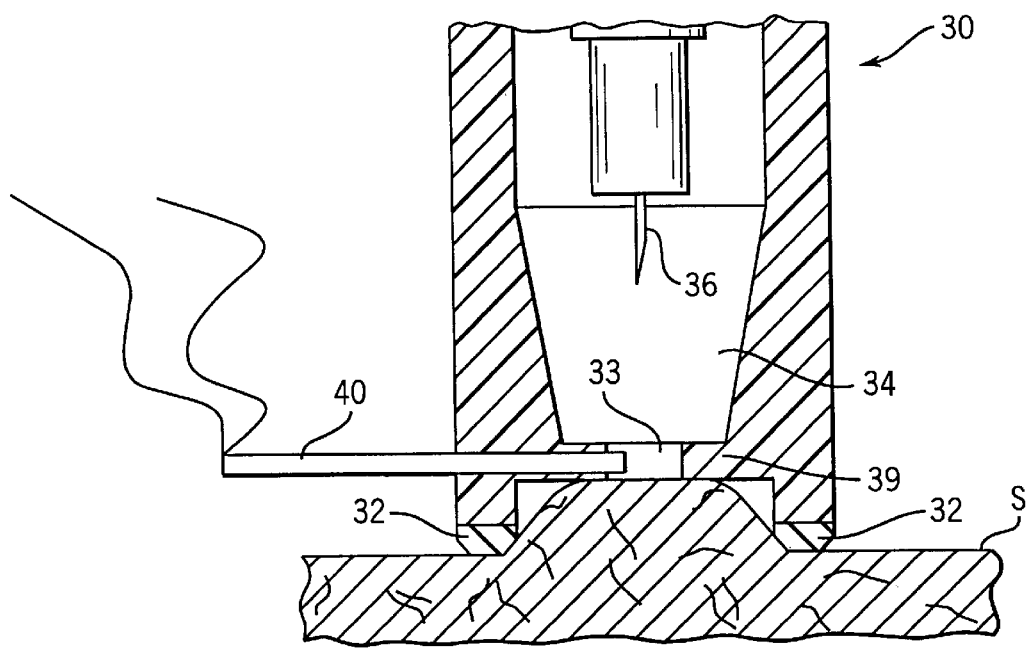
FIG. 2 is a schematic diagram illustrating how a vacuum causes a portion of the skin to become stretched prior to the formation of an opening in the skin from which the sample of blood is extracted.
Figure 4:
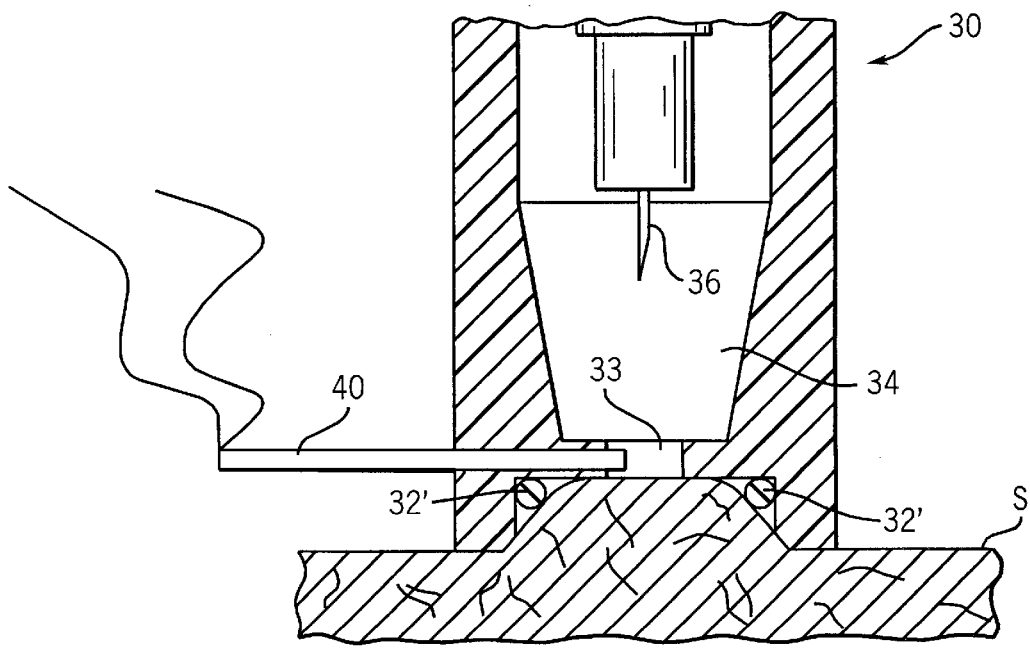
FIG. 4 is a schematic diagram illustrating an alternative seal for the vacuum of the device of the present invention.

Operation of the blood extraction device 10 will now be described. Referring now to FIGS. 1, 2 and 3, the nosepiece 30 of the lancing assembly 16 is applied to the surface of the skin, designated herein by the letter "S". The end of the nosepiece 30 that contacts the skin is equipped with a seal 32. The purpose of the seal 32 is to prevent air from leaking into blood extraction chamber 34, so that the vacuum pump 14 can provide sufficient suction action for increasing the availability of blood to the area of the skin from which the sample is to be extracted, stretching the skin, and extracting the sample of blood from the unobstructed opening in the skin. The seal 32 surrounds an opening 33 in the nosepiece 30. The opening 33 in the nosepiece allows communication between the surface of the skin and a blood extraction chamber 34 in the nosepiece 30. The seal 32 is preferably made of a rubber or an elastomeric material. FIG. 4 illustrates an alternative position for the seal 32. In FIG. 4, the seal is designated by the reference numeral 32'. The remaining parts of FIG. 4 are the same as those of FIG. 2, and, accordingly, retain the same reference numerals as were used in FIG. 2.

It has been discovered that an improved design and construction of the nosepiece 30 can provide enhanced collection of blood from the unobstructed opening in the skin. In FIG. 2, it is shown that the interior walls of the nosepiece form a shape that is essentially cylindrical. While this design is capable of providing adequate performance in the method of this invention, it has been discovered that by changing the construction of the interior cavity of the nosepiece, collection of blood can be accelerated.

A nosepiece assembly 3000 is illustrated in FIG. 11. The nosepiece assembly 3000 comprises a nosepiece 3001 and a seal 3002. The nosepiece 3001 comprises a lower base 3004 having an opening 3005 therein. Above the lower base 3004 is an upper base 3006 having an opening 3007 therein. The features of the exterior of the nosepiece, other than the lower base 3004 and the upper base 3006, are not critical to this invention, and one of ordinary skill in the art can design the exterior walls of the nosepiece in any manner that does not adversely affect the operation of the nosepiece of this invention. The features of the interior of the nosepiece, the lower base 3004, the upper base 3006, and, in some cases, the seal 3002 are critical and, consequently, they will be described in greater detail. An interior wall 3008 encloses a cavity 3010 of the nosepiece 3001. It is critical that the interior wall 3008 of the nosepiece 3001 be structured in such a manner that the opening 3007 in the upper base 3006 be of an equal or smaller area than the opening 3005 in the lower base 3004. It is desired that the area of the opening 3007 be reduced to as small of a size as possible, but not so small as to interfere with the collection of blood by a glucose monitor (see FIG. 2) or with the path of a lancet. An optional rim 3012 can surround the opening 3007 in the upper base 3006.

There a several ways of causing the area of the opening 3007 to be less than the area of the opening 3005. As shown in FIG. 11, the interior wall 3008 can be tapered so as to bring about a reduction in the area of the opening 3007. The tapering can begin at any point along the interior wall 3008 of the nosepiece 3001. If the tapered portion runs all the way from the beginning of the tapered portion to the upper base 3006, the optional rim 3012 still have a depth of zero, and thus be eliminated from the nosepiece. Alternatively, the area of the opening 3007 can merely be made smaller than the area of the opening 3005, such as through the use of step-wise cylindrical sections.

Ports 3014 and 3016 can be included in the nosepiece 3001 to give the cavity 3010 more exposure to a vacuum, if needed.

In order to more accurately describe the construction of the nosepiece assembly 3000, reference points, designated by alphabetical letters, have been placed on FIG. 11 so that typical distances between these reference points can be disclosed. The optional rim 3012 has a depth designated by the line "ab". This depth typically ranges from 0 to about 1.5 mm, preferably from 0 to about 1.0 mm. The opening 3007 in the upper base 3006 has a major dimension designated by the line "cd". The area of the opening 3007 typically ranges from about 1 to about 500 mm$^2$, preferably from about 1 to about 150 mm$^2$. The opening 3005 in the lower base 3004 has a major dimension designated by the line "ef". The area of the opening 3005 typically ranges from about 10 to about 500 mm$^2$, preferably from about 50 to about 150 mm$^2$. The distance from the lowermost point of the rim 3012 to to lowermost point of the seal 3002 (hereinafter "rim-to-seal distance") is designated by the line "bg". This distance typically ranges from about 1.5 to about 8.0 mm, preferably from about 3 to about 6 mm. It is preferred that the distance be selected so that the skin, when stretched into the nosepiece 3001, comes as close as possible to the rim 3012 or the upper base 3006 of the nosepiece 3001. If the rim 3012 is not present, the point "d" will be located at the level of the upper base 3006. The thickness of the seal 3002 is represented by the line "eh". The width of the sealing surface and the width of the sealed surface of the lower base 3004 are designated by the line "hj". One of ordinary skill in the art would have sufficient expertise to optimize the dimensions of the nosepiece without undue experimentation. Additional details regarding the nosepiece 3001 and the seal 3002 are dealt with in the examples.

This improved nosepiece has several advantages. The improved design and construction of the nosepiece can provide enhanced collection of blood from the unobstructed opening in the skin. The nosepiece brings about a better seal to the body than do the nosepieces previously used. A better seal reduces the amount of vacuum leakage, with the result that a less expensive vacuum pump can be used. In addition, the improved nosepiece allows a seal to be maintained on those individuals having excessively hairy skin.

The switch 22 is actuated, typically by being pressed, thereby activating the electronics 20, which starts the vacuum pump 14. The vacuum pump 14 then provides a suction action. The suction action of the vacuum pump 14 causes the skin circumscribed by the seal 32 to become engorged with blood. Engorgement of the skin with blood is accompanied by a stretching of and rising up of the skin up to opening 33.

After an appropriate period of time, which is typically pre-set by the programmer of the electronics, the lancing assembly 16 is triggered, thereby causing the lancet 36 to penetrate the skin that has risen up to the opening 33 and that is engorged with blood. The lancet 36 is preferably triggered automatically, by a solenoid valve 38 that causes a vacuum-actuateed piston (not shown) to trigger the lancet 36. The lancet 36 is then retracted, preferably automatically. Thereupon, the blood flows out of the unobstructed opening resulting from the lancet 36, and, aided by the vacuum generated by the vacuum pump 14, is collected. When sufficient blood has been collected or a pre-set time interval has passed, the electronics 20 causes the vacuum pump 14 to stop. The device 10 can then be removed from the surface of the skin after another solenoid valve (not shown because it is hidden under solenoid valve 38) is opened to vent the vacuum to allow ease of removal of the device from the surface of the skin. Solenoid valves suitable for use with the apparatus described herein are commercially available from The Lee Company, Essex, Conn., and have the part number LHDA051111H.

The blood is preferably directly collected on the application zone of a glucose detector, e.g., a reflectance strip or biosensor. The blood can then be used as the sample for a determination of glucose concentration in blood. Alternatively, the blood can be collected by other collection devices, such as, for example, a capillary tube or absorbent paper.

The apparatus of the present invention can include a glucose detector for analyzing the blood sample extracted by the apparatus. Glucose detectors are well-known in the art. With respect to glucose monitoring, there are two major categories of glucose detectors—reflectometers and biosensors. Representative examples of reflectometers suitable for this invention are described in U.S. Pat. No. 4,627,445, incorporated herein by reference. Representative examples of biosensors suitable for this invention are described in U.S. Pat. No. 5,509,410, incorporated herein by reference.

The glucose detector is preferably disposed in the nosepiece 30 of the lancing assembly 16. The glucose detector must be located at a position sufficiently close to the site of blood extraction so that the quantity of extracted blood collected will be sufficient to carry out a standard glucose monitoring test. Typically, this distance will preferably be no more than 5 mm from the site of blood extraction, more preferably no more than 3 mm from the site of blood extraction, most preferably no more than 1 mm from the site of blood extraction. Care must be taken in the placement of the glucose detector so that the detector does not adversely affect the vacuum, when a vacuum is employed to aid in the extraction of blood. In addition, the glucose detector 40 should be modified, if necessary, so that the blood collected in the collection zone of the glucose detector is capable of being used to activate the glucose detector.

FIG. 2 also illustrates a manner for disposing a glucose detector 40 in the nosepiece 30 of the lancing assembly 16.

Figure 5:
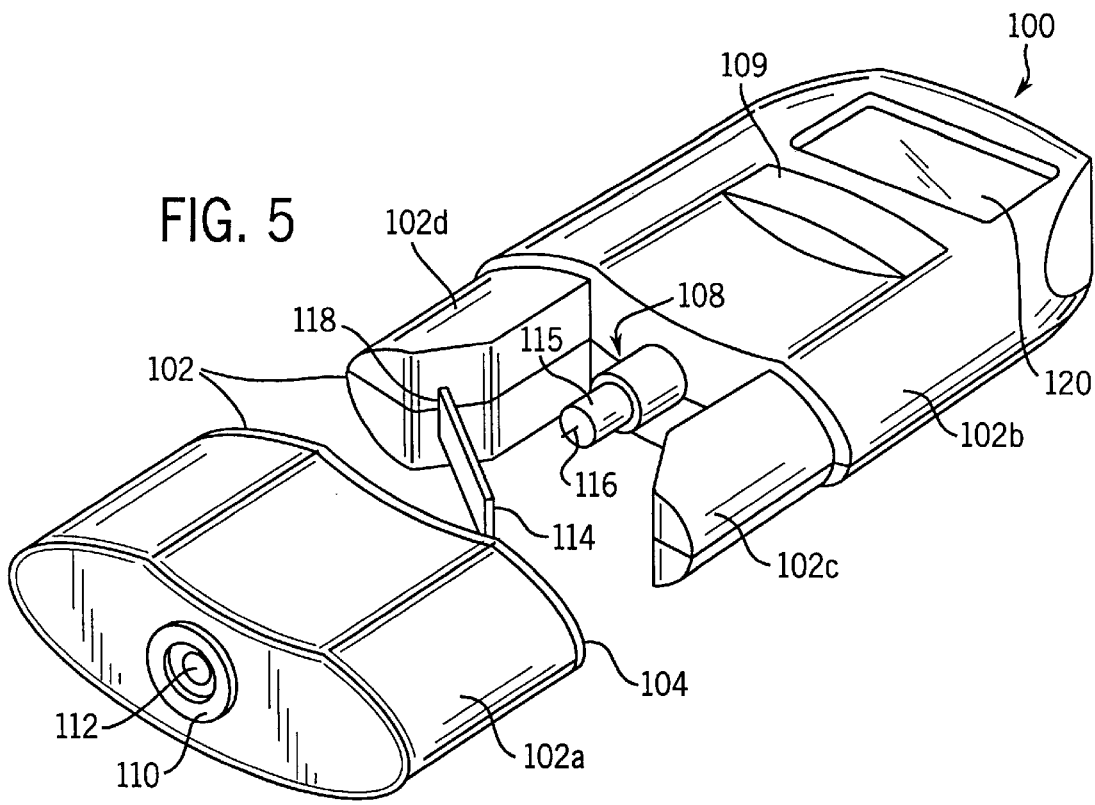
FIG. 5 is a perspective view of an embodiment of the apparatus of this invention. In this figure, the housing of the apparatus is open.

FIGS. 5, 6, 7, 8, 9, and 10 illustrate various alternative embodiments of the apparatus of this invention. In FIG. 5, blood extraction device 100 comprises a housing 102. The housing 102 is separable into two portions, a receiving portion 102a and a projecting portion 102b. A gasket 104 is provided to seal the portions 102a and 102b of the housing 102 and to aid in separation of the receiving portion 102a from the projecting portion 102b. The receiving portion 102a forms a tight fit with the projecting portion 102b by means of friction. Projecting elements 102c and 102d are used to guide the projecting portion 102b into the receiving portion 102a. Disposed within the housing 102 are a vacuum pump (not shown), a lancing assembly 108, a battery (not shown), and electronics (not shown). A switch 109 is provided to activate the electronics. The vacuum pump is connected to the lancing assembly 108 by an evacuation tube (not shown). A check valve (not shown) is placed between the vacuum pump and the lancing assembly 108.

During the process of obtaining the sample, the receiving portion 102a and the projecting portion 102b are fitted tightly together. The area of the receiving portion 102a of the housing 102 of the device 100 that is to contact the skin is equipped with a seal 110. The seal 110 surrounds an opening 112 in the receiving portion 102a. The opening 112 in the receiving portion 102a allows communication between the surface of the skin and a blood extraction chamber adjacent to a glucose detector 114, shown here in the shape of a strip. When in use, the device 100 is positioned so that the lancing assembly 108 is placed over the region on the surface of the skin from which the sample is to be obtained. In order to obtain the sample of blood, the receiving portion 102a of the housing 102 of the device 100 is placed against the skin, whereby the seal 110 allows a satisfactory vacuum to be effected. The switch 109 is actuated, typically by being pressed, thereby activating the electronics, which starts the vacuum pump. The vacuum pump then provides a suction action. The suction action of the vacuum pump causes the skin circumscribed by the seal 110 to become engorged with blood. Engorgement of the skin with blood is accompanied by a stretching of and rising up of the skin up to the opening 112. After an appropriate period of time, which is typically pre-set by the programmer of the electronics, the lancing assembly 108 is triggered, thereby causing the lancet 116 to penetrate the skin that has risen up to the opening 112 and that is engorged with blood. The lancet 116 is preferably triggered automatically, by a solenoid valve (not shown) that causes a vacuum-actuated piston (not shown) to trigger the lancet 116. The remaining steps of the process relating to collection of a sample of blood are substantially similar to the steps described in the embodiment shown in FIGS. 1, 2, 3, and 4.

In the embodiment shown in FIG. 5, the glucose detector 114 is inserted into a slot 118 in the projecting portion 102b of the housing 102. The receiving portion 102a of the housing 102 causes the glucose detector 114 to be moved into its proper position for testing. The results obtained from the glucose detector 114 can be displayed on a screen 120, typically a conventional liquid crystal digital display. The receiving portion 102a is separated from the projecting portion 102b when the lancet 116 or glucose detector 114 is being replaced. The receiving portion 102a is fitted tightly to the projecting portion 102b during the process of obtaining a sample of blood.

The relative positions of the vacuum pump, the battery, the electronics, the evacuation tube, the check valve, the solenoid valves, and the vacuum-actuated piston are substantially similar to the relative positions of these components as described in the embodiments shown in FIGS. 1 and 2.

Figure 6:
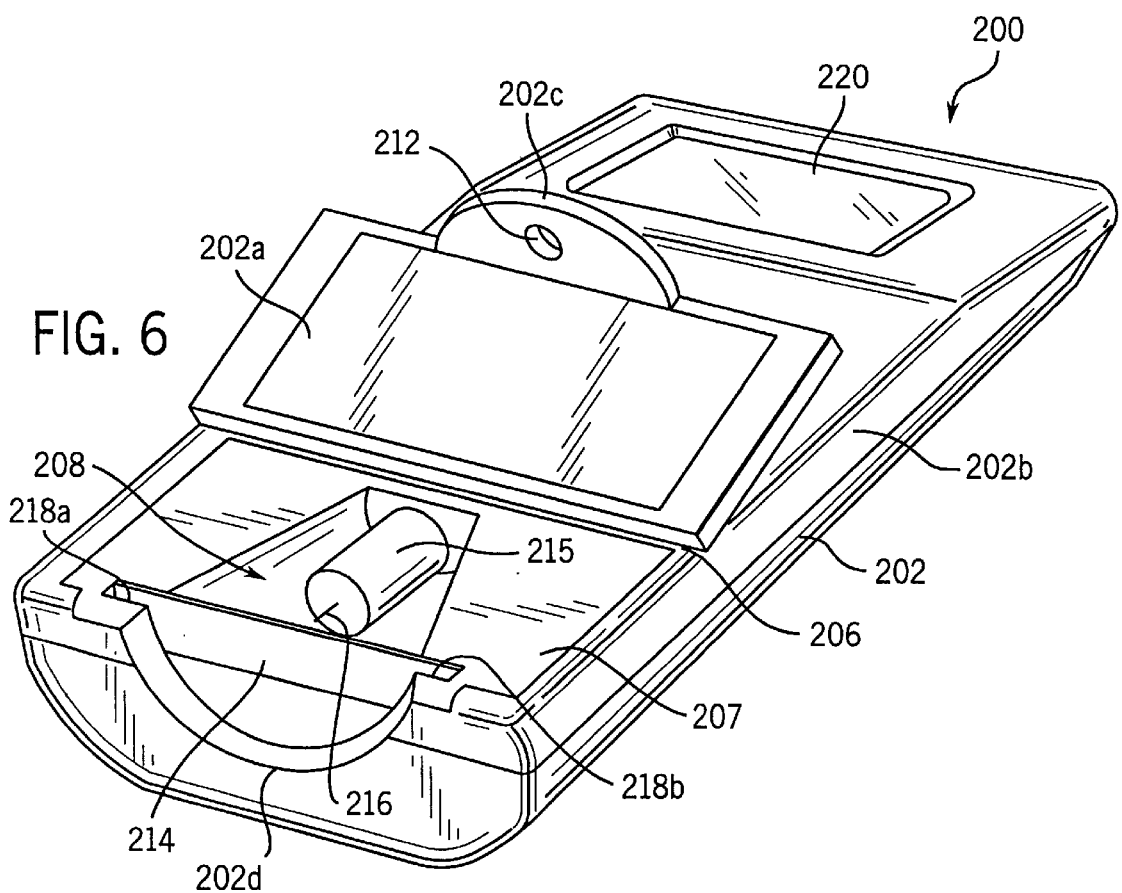
FIG. 6 is a perspective view of an embodiment of the apparatus of this invention. In this figure, the housing of the apparatus is open.

In FIG. 6, blood extraction device 200 comprises a housing 202. The housing 202 comprises a door portion 202a that is attached to the remaining portion 202b of the housing 202 by a hinge 206. A gasket 207 is provided to seal the housing 202 when the door portion 202a is closed. The door portion 202a can be closed by pivoting it around the hinge 206. When the door portion 202a is closed, the convex portion 202c of the door portion 202a fits precisely into the concave portion 202d of the remaining portion 202b of the housing 202. The remaining edges of the door portion 202a fit tightly against the remaining edges of the remaining portion 202b of the housing 202. Disposed within the housing 202 are a vacuum pump (not shown), a lancing assembly 208, a battery (not shown), and electronics (not shown). A switch (not shown) is provided to activate the electronics. The vacuum pump is connected to the lancing assembly 208 by an evacuation tube (not shown). A check valve (not shown) is placed between the vacuum pump and the lancing assembly 208.

During the process of obtaining the sample, the door portion 202a is closed. The area of the door portion 202a of the housing 202 of the device 200 that is to contact the skin is equipped with a seal (not shown). The seal surrounds an opening 212 in the door portion 202a. The opening 212 in the door portion 202a allows communication between the surface of the skin and a blood extraction chamber adjacent to a glucose detector 214, shown here in the shape of a strip. When in use, the device 200 is positioned so that the lancing assembly 208 is placed over the region on the surface of the skin from which the sample is to be obtained. In order to obtain the sample of blood, the door portion 202a of the housing 202 of the device 200 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 212. After an appropriate period of time, which is typically pre-set by the programmer of the electronics, the lancing assembly 208 is triggered, thereby causing the lancet 216 to penetrate the skin that has risen up to the opening 212 and that is engorged with blood. The lancet 216 is preferably triggered automatically, by a solenoid valve (not shown) that causes a vacuum-actuated piston (not shown) to trigger the lancet 216. The remaining steps of the process relating to collection of a sample of blood are substantially similar to the steps described in the embodiment shown in FIGS. 1, 2, 3, and 4.

In the embodiment shown in FIG. 6, the glucose detector 214 is inserted into slots 218a and 218b of the housing 202. The results obtained from the glucose detector 214 can be displayed on screen 220, typically a conventional liquid crystal digital display. The door portion 202a is opened when the lancet 216 or glucose detector 214 is being replaced. The door portion 202a is closed during the process of obtaining a sample of blood.

The relative positions of the vacuum pump, the battery, the electronics, the switch, the evacuation tube, the check valve, the seal, the solenoid valves, and the vacuum-actuated piston are substantially similar to the relative positions of these components as described in the embodiments shown in FIGS. 1 and 2.

In FIG. 7, blood extraction device 300 comprises a housing 302. The housing 302 comprises a door portion 302a that is attached to the remaining portion 302b of the housing 302 by a hinge 306. A gasket 307 is provided to seal the housing 302 when the door portion 302a is closed. The door portion 302a can be closed by pivoting it around the hinge 306. When the door portion 302a is closed, the convex portion 302c of the door portion 302a fits precisely into the concave portion 302d of the remaining portion 302b of the housing 302. The remaining edges of the door portion 302a fit tightly against the remaining edges of the remaining portion 302b of the housing 302. Disposed within the housing 302 are a vacuum pump (not shown), a lancing assembly 308, a battery (not shown), and electronics (not shown). A switch (not shown) is provided to activate the electronics. The vacuum pump is connected to the lancing assembly 308 by an evacuation tube (not shown). A check valve (not shown) is placed between the vacuum pump and the lancing assembly 308.

During the process of obtaining the sample, the door portion 302a is closed. The area of the door portion 302a of the housing 302 of the device 300 that is to contact the skin is equipped with a seal (not shown). The seal surrounds an opening 312 in the door portion 302a. The opening 312 in the door portion 302a allows communication between the surface of the skin and a blood extraction chamber adjacent to a glucose detector 314, shown here in the shape of a strip. When in use, the device 300 is positioned so that the lancing assembly 308 is placed over the region on the surface of the skin from which the sample is to be obtained. In order to obtain the sample of blood, the door portion 302a of the housing 302 of the device 300 is placed against the skin, whereby the seal allows a satisfactory vacuum to be effected. The switch is actuated, typically by being pressed, thereby activating the electronics, which starts the vacuum pump. The vacuum pump then provides a suction action The suction action of the vacuum pump causes the skin circumscribe by the seal to become engorged with blood. Engorgement of the skin with blood is accompanied by a stretching of and rising up of the skin up to the opening 312. After an appropriate period of time, which is typically pre-set by the programmer of the electronics, the lancing assembly 308 is triggered, thereby causing the lancet 316 to penetrate the skin that has risen up to the opening 312 and that is engorged with blood. The lancet 316 is preferably triggered automatically, by a solenoid valve (not shown) that causes a vacuum-actuated piston (not shown) to trigger the lancet 316. The remaining steps of the process relating to collection of a sample of blood are substantially similar to the steps described in the embodiment shown in FIGS. 1, 2, 3, and 4.

In the embodiment shown in FIG. 7, the glucose detector 314 is inserted into a slot 318 of the housing 302. The results obtained from the glucose detector 314 can be displayed on screen 320, typically a conventional liquid crystal digital display. In FIG. 7, connections 322 for the electronics are shown. The door portion 302a is opened when the lancet 316 or glucose detector 314 is being replaced. The door portion 302a is closed during the process of obtaining a sample of blood.

The relative positions of the vacuum pump, the battery, the electronics, the switch, the evacuation tube, the check valve, the seal, the solenoid valves, and the vacuum-actuated piston are substantially similar to the relative positions of these components as described in the embodiments shown in FIGS. 1 and 2.

In FIG. 8, blood extraction device 400 comprises a housing 402. The housing 402 comprises a door portion 402a that is attached to the remaining portion 402b of the housing 402 by a hinge 406. A gasket 407 is provided to seal the housing 402 when the door portion 402a is closed. The door portion 402a can be closed by pivoting it around the hinge 406. When the door portion 402a is closed, the convex portions 402c and 402d of the door portion 402a fit precisely into the concave portions 402e and 402f, respectively, of the remaining portion 402b of the housing 402. The remaining edges of the door portion 402a fit tightly against the remaining edges of the remaining portion 402b of the housing 402. Disposed within the housing 402 are a vacuum pump (not shown), a lancing assembly 408, a battery (not shown), and electronics (not shown). A switch 409 is provided to activate the electronics. The vacuum pump is connected to the lancing assembly 408 by an evacuation tube (not shown). A check valve (not shown) is placed between the vacuum pump and the lancing assembly 408.

During the process of obtaining the sample, the door portion 402a is closed. The area of the door portion 402a of the housing 402 of the device 400 that is to contact the skin is equipped with a seal (not shown). The seal surrounds an opening 412 in the door portion 402a. The opening 412 in the door portion 402a allows communication between the surface of the skin and a blood extraction chamber adjacent to a glucose detector 414, shown here in the shape of a strip. When in use, the device 400 is positioned so that the lancing assembly 408 is placed over the region on the surface of the skin from which the sample is to be obtained. In order to obtain the sample of blood, the door portion 402a of the housing 402 of the device 400 is placed against the skin, whereby the seal allows a satisfactory vacuum to be effected. The switch 409 is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 412. After an appropriate period of time, which is typically pre-set by the programmer of the electronics, the lancing assembly 408 is triggered, thereby causing the lancet 416 to penetrate the skin that has risen up to the opening 412 and that is engorged with blood. The lancet 416 is preferably triggered automatically, by a solenoid valve (not shown) that causes a vacuum-actuated piston (not shown) to trigger the lancet 416. The remaining steps of the process relating to collection of a sample of blood are substantially similar to the steps described in the embodiment shown in FIGS. 1, 2, 3, and 4.

In the embodiment shown in FIG. 8, the glucose detector 414 is inserted into a slot 418 of the housing 402. In this embodiment, it is shown that glucose detector 14 can be rotated 90° between two positions to simplify insertion and replacement thereof. The results obtained from the glucose detector 414 can be displayed on screen 420, typically a conventional liquid crystal digital display. The door portion 402a is opened when the lancet 416 or glucose detector 414 is being replaced. The door portion 402a is closed during the process of obtaining a sample of blood.

The relative positions of the vacuum pump, the battery, the electronics, the evacuation tube, the check valve, the seal, the solenoid valves, and the vacuum-actuated piston are substantially similar to the relative positions of these components as described in the embodiments shown in FIGS. 1 and 2.

In FIG. 9, blood extraction device 500 comprises a housing 502. The housing 502 comprises a cover portion 502a that is attached to the remaining portion 502b of the housing 502 by a hinge 506. A gasket 507 is provided to seal the housing 502 when the cover portion 502a is closed. The cover portion 502a can be closed by pivoting it around the hinge 506. When the cover portion 502a is closed, edges 502c of the cover portion 502a tightly fit against edges 502d of the remaining portion 502b of the housing 502. Disposed within the housing 502 are a vacuum pump (not shown), a lancing assembly 508, a battery (not shown), and electronics (not shown). A switch (not shown) is provided to activate the electronics. The vacuum pump is connected to the lancing assembly 508 by an evacuation tube (not shown). A check valve (not shown) is placed between the vacuum pump and the lancing assembly 508.

During the process of obtaining the sample, the cover portion 502a is closed. The cover portion 502a of the housing 502 of the device 500 that is to contact the skin is equipped with a seal 511. The seal 511 surround an opening 512 in the cover portion 502a. The opening 512 in the cover portion 502a allows communication between the surface of the skin and a blood extraction chamber adjacent to a glucose detector 514, shown here in the shape of a strip. When in use, the device 500 is positioned so that the lancing assembly 508 is placed over the region on the surface of the skin from which the sample is to be obtained. In order to obtain the sample of blood, the cover portion 502a of the housing 502 of the device 500 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 512. After an appropriate period of time, which is typically pre-set by the programmer of the electronics, the lancing assembly 508 is triggered, thereby causing the lancet 516 to penetrate the skin that has risen up to the opening 512 and that is engorged with blood. The lancet 516 is preferably triggered automatically, by a solenoid valve (not shown) that causes a vacuum-actuated piston (not shown) to trigger the lancet 516. The remaining steps of the process relating to collection of a sample of blood are substantially similar to the steps described in the embodiment shown in FIGS. 1, 2, 3, and 4.

In the embodiment shown in FIG. 9, the glucose detector 514 is inserted into a slot 518 of the housing 502. The results obtained from the glucose detector 514 can be displayed on screen 520, typically a conventional liquid crystal digital display. The cover portion 502a is opened when the lancet 516 or glucose detector 514 is being replaced. The cover portion 502a is closed during the process of obtaining a sample of blood.

The relative positions of the vacuum pump, the battery, the electronics, the switch, the evacuation tube, the check valve, the solenoid valves, and the vacuum-actuated piston are substantially similar to the relative positions of these components as described in the embodiments shown in FIGS. 1 and 2.

In FIG. 10, blood extraction device 600 comprises a housing 602. The housing 602 comprises a cover portion 602a that is attached to the remaining portion 602b of the housing 602 by a hinge 606. A gasket 607 is provided to seal the housing 602 when the cover portion 602a is closed. The cover portion 602a can be closed by pivoting it around the hinge 606. When the cover portion 602a is closed, edges 602c of the cover portion 602a tightly fit against edges 602d of the remaining portion 602b of the housing 602. Disposed within the housing 602 are a vacuum pump (not shown), a lancing assembly 608, a battery (not shown), and electronics (not shown). A switch 609 is provided to activate the electronics. The vacuum pump is connected to the lancing assembly 608 by an evacuation tube (not shown). A check valve (not shown) is placed between the vacuum pump and the lancing assembly 608.

During the process of obtaining the sample, the cover portion 602a is closed. The cover portion 602a of the housing 602 of the device 600 that contacts the skin is equipped with a seal 611. The seal 611 surrounds an opening 612 in the cover portion 602a. The opening 612 in the cover portion 602a allows communication between the surface of the skin and a blood extraction chamber adjacent to a glucose detector 614, shown here in the shape of a strip. When in use, the device 600 is positioned so that the lancing assembly 608 is placed over the region on the surface of the skin from which the sample is to be obtained. In order to obtain the sample of blood, the cover portion 602a of the housing 602 of the device 600 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 612. After an appropriate period of time, which is typically pre-set by the programmer of the electronics, the lancing assembly 608 is triggered, thereby causing the lancet 616 to penetrate the skin that has risen up to the opening 612 and that is engorged with blood. The lancet 616 is preferably triggered automatically, by a solenoid valve (not shown) that causes a vacuum-actuated piston (not shown) to trigger the lancet 616. The remaining steps of the process relating to collection of a sample of blood are substantially similar to the steps described in the embodiment shown in FIGS. 1, 2, 3, and 4.

In the embodiment shown in FIG. 10, the glucose detector 614 is inserted into a slot 618 of the housing 602. The results obtained from the glucose detector 614 can be displayed on screen 620, typically a conventional liquid crystal digital display. The cover portion 602a is opened when the lancet 616 or glucose detector 614 is being replaced. The cover portion 602a is closed during the process of obtaining a sample of blood.

The relative positions of the vacuum pump, the battery, the electronics, the switch, the evacuation tube, the check valve, the solenoid valves, and the vacuum-actuated piston are substantially similar to the relative positions of these components as described in the embodiments shown in FIGS. 1 and 2.

In each of the embodiments shown in the foregoing FIGS. 5, 6, 7, 8, 9, and 10, the housing, vacuum pump, lancing assembly, battery, electronics, evacuation tube, check valve, nosepiece, seal, opening, blood extraction chamber, lancet, and solenoid valve can be made of the same materials as the corresponding components of the apparatus shown in FIGS. 1, 2, and 3. The gaskets 104, 207, 307, 407, 507, and 607 can be made of the same material as the seal. The components shown in the foregoing FIGS. 5, 6, 7, 8, 9, and 10 function in the same manner as do the corresponding components of the apparatus shown in FIGS. 1, 2, and 3.

It should be noted that the designs of the various housings shown in FIGS. 5, 6, 7, 8, 9, and 10 can be modified without substantially affecting the functioning of the components disposed within the housing or on the surface of the housing. For example, the shapes of the housings, the shapes of the door portions of the housings, the shapes of the cover portions of the housings, and the shapes of the remaining portions of the housings can be modified without departing from the scope and spirit of this invention.

This invention provides numerous advantages over blood extraction devices of the prior art. Among these advantages are the following:

1. Ability to use parts of the body, other than the finger, as a site for the extraction of blood;
2. Reduction of pain by eliminating the need to lance the finger;
3. Increase in speed of collection of blood samples by means of pretreatment comprising a combination of stretching of the skin in conjunction with heat or vacuum or both heat and vacuum;
4. Incorporation of glucose detector in apparatus for extracting the blood sample.

The following examples illustrate various features of the present invention but is not intended to in any way limit the scope of the invention as set forth in the claims. In the following examples, the term "pierce" and forms thereof and the term "puncture" and forms thereof are used interchangeably. Although the expression "glucose detector" is used herein, one of ordinary skill in the art will recognize that the apparatus and methods of the present invention can also be used to perform other diagnostic tests.

EXAMPLES

Example 1

This example illustrates that greater volumes of blood can be extracted and collected by applying a vacuum, pulsed or continuous, after piercing than can be extracted and collected when no vacuum is applied. No vacuum was applied prior to piercing.

Each of four people had his forearm (dorsal forearm) punctured four times (at four different positions on the forearm) with a "BD ULTRA-FINE" lancet in a "MEDIS-ENSE" lancet assembly (Model no. 97101) at two different levels of vacuum (−2.5 psig and −5.0 psig) and for each different vacuum pulsing frequencies (0, 0.2, 0.8, 3.2, 12.8, 25, 100 hertz). The vacuum was applied with a pipette tip having a diameter of 8 mm ("RAININ RT-200"). Four control runs without a vacuum were also carried out (one puncture per person). A total of 60 punctures per person were carried out. Accordingly, it can be seen that a total of 240 runs were carried out.

The vacuum was applied for a duration of 30 seconds after puncturing. Blood was collected into capillary tubes. In the control runs, the samples were extracted and collected 30 seconds after puncturing. The amount of blood collected was determined by measuring the length of blood in the tubes. The percentage of collections in which the volume of blood collected exceeded 1.0 µL was calculated. Sensation of pain was also recorded. The following pain scores were used:

Pain of 1=person did not feel anything or not sure if anything was felt Pain of 2=person felt definite prick, not as painful as piercing of finger by standard finger lancet Pain of 3=person felt definite pain, approximately equal to a piercing of finger by standard finger lancet Blood collection results are set forth in TABLE I.

TABLE I

| Frequency (hertz) | Average volume of blood sample collected at −2.5 psig (µL) | Percent of samples having > 1 µL of blood collected at −2.5 psig | Average volume of blood sample collected at −5.0 psig (µL) | Percent of samples having >1 µL of blood collected at −5.0 psig |
|---|---|---|---|---|
| 0 (Continuous) | 1.6 | 69 | 3.1 | 94 |
| 0.2 | 1.1 | 44 | 3.0 | 94 |
| 0.8 | 1.1 | 63 | | 75 |
| 3.2 | 1.5 | 56 | 3.8 | 75 |
| 12.8 | 1.8 | 75 | 3.1 | 100 |
| 25 | 2.3 | 75 | 3.2 | 94 |
| 100 | 2.4 | 51 | 2.7 | 88 |

With no vacuum, average volume of blood collected was 0.8 µL and 31% of the samples collected contained more than 1 µL. The pain results we re as follows:

pain of 1=81% pain of 2=17% pain of 3=2%

The control runs (no vacuum) provided much lower volumes of blood collected than did the runs where vacuum was applied. Increased vacuum resulted in higher volumes of blood extracted. The pain was minimal, with only 2% of the punctures resulting in pain comparable to that resulting from a piercing of the finger.

Example 2

This example illustrates that application of vacuum prior to piercing as well as after piercing results in a greater volume of blood extracted than does the application of vacuum only after piercing.

Each of four people had his forearm (dorsal forearm, middle of forearm) punctured sixteen times (at sixteen different positions on the forearm) with a "BD ULTRA-FINE" lancet in a modified "MEDISENSE" lancet assembly at four different levels of vacuum. The four levels of vacuum used were −2.5, −5.0, −7.5, and −10.0 psig. The "MEDIS-ENSE" lancet device was modified to allow vacuum to be pulled through the lancet assembly. Four punctures per person were carried out at each of the four levels of continuous vacuum. Accordingly, it can be seen that a total of 64 runs were carried out.

Prior to puncturing, the vacuum was applied for a period of 30 seconds; subsequent to puncturing, the vacuum was applied for a period of 30 seconds. The skin was under vacuum at the time the lancet was triggered. After the lancet was triggered, the lancet assembly was removed, and the vacuum was used to apply the same level of vacuum that had been used for the vacuum prior to puncturing. The vacuum, both prior to puncturing and subsequent to puncturing, was applied with a pipette tip having a diameter of 8 mm ("RAININ RT-200"). The pipette tip of the vacuum device was held level to the plane of the skin. Blood was then collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE II.

TABLE II

| Vacuum level (psig) | Average volume of blood sample collected (µL) | Percent of samples having >1 µL of blood collected |
|---|---|---|
| −2.5 | 4.6 | 94 |
| −5.0 | 7.8 | 100 |
| −7.5 | 9.2 | 100 |
| −10.0 | 14.0 | 100 |

The pain results were as follows:

pain of 1=58% pain of 02=31% pain of 3=11%

A nearly linear relationship between level of vacuum and volume of blood collected was observed. The average volume of blood collected with vacuum applied prior and after piercing was approximately twice that collected with vacuum applied only after piercing without vacuum applied prior to piercing. See the results of Example 1 for this comparison (7.8 µL vs. 3.1 µL). The volume of blood collected was always above 1 µL for all levels of vacuum, except −2.5 psig.

Example 3

This example illustrates that localized heating of the area to be pierced followed by vacuum after piercing results in a greater volume of blood being extracted than does extraction with only vacuum after piercing.

Each of four people had his forearm (dorsal forearm, middle of forearm) punctured eight times (at eight different positions on the forearm) with a "BD ULTRA-FINE" lancet in a "MEDISENSE" lancet assembly with heat applied (45° C.) prior to piercing for two different time periods, 15 seconds and 60 seconds. A total of 32 runs were carried out, 16 runs where the pre-heating duration was 15 seconds and 16 runs where the pre-heating duration was 60 seconds.

Heat was applied with a heating block, which was an aluminum block having a square face covered with a "KAPTON" film heater element controlled by an "OMEGA" DP41 temperature controller using a T-type thermocouple.

Vacuum was applied after each puncturing for 30 seconds at −5.0 psig. Blood was collected into capillary tubes. The amount of blood collected was determined by measuring the length of blood in the tubes. The percentage of collections in which the volume of blood collected exceeded 1.0 μL was calculated. Pain was also tracked. Blood collection results are set forth in TABLE III.

TABLE III

| Pre-piercing heating duration (seconds) | Average volume of blood samples collected (μL) | Percent of samples having >1 μL of blood collected |
|---|---|---|
| 15 | 6.91 | 94 |
| 60 | 11.6 | 100 |

The pain results were as follows:
 pain of 1=91%
 pain of 2=9%
 pain of 3=0%

The average volume of blood collected using a pre-heating duration of 15 seconds was more than twice the average volume of blood collected at a post-puncturing vacuum level of −5.0 psig., with no pre-heating. See the results of Example 1 for this comparison (6.91 μL vs. 3.1 μL). The average volume of blood collected using a pre-heating duration of 60 seconds was approximately four times the average volume of blood collected at a post-puncturing vacuum level of −5.0 psig, with no pre-heating. See the results of Example 1 for this comparison (11.6 μL vs. 3.1 μL).

Example 4

This example illustrates the effect that stretching the skin upwardly with a vacuum has on the extraction of blood.

Each of four people had his forearm (dorsal forearm, middle of forearm) punctured eight times (at eight different positions on the forearm) with a "BD ULTRA-FINE" lancet in a "MEDISENSE" lancet assembly. Vacuum was applied for a period of 30 seconds prior to puncturing at −5.0 psig using two different vacuum fixtures. The first fixture was a 15 mm diameter vacuum fixture (i.e., a hollow cylindrical tube) used without a net strung across the opening of the tube. The second fixture was a 15 mm diameter vacuum fixture (i.e., a hollow cylindrical tube) used with a net strung across the opening of the lube. The net prevented skin from being raised up into the vacuum fixture. The same vacuum fixture used prior to puncturing was applied for a period of 30 seconds after puncturing. The fixture was held level with the plane of the skin. Four punctures were carried out per person per condition (without net, with net). Accordingly, it can be seen that a total of 32 runs were carried out. Blood was collected into capillary tubes. The amount of blood collected was determined by measuring the length of blood in the tubes. The percentage of collections in which the volume of blood collected exceeded 1.0 μL was calculated. Sensation of pain was also recorded. Blood collection results are set forth in TABLE IV.

TABLE IV

| Net across nosepiece | Average volume of blood sample collected (μL) | Percent of samples having >1 μL of blood collected |
|---|---|---|
| No | 5.2 | 87 |
| Yes | 0.6 | 19 |

The pain results were as follows:
 pain of 1=94%
 pain of 2=6%
 pain of 3=0%

The magnitude of the difference in volume of blood collected and success rates (i.e., percent of samples having >1 μL of blood collected) between the condition of stretching the skin in combination with a vacuum and the condition of not stretching the skin in combination with a vacuum was unexpected. The pain scores were low. This example demonstrates that the combination of skin stretching and applied vacuum significantly increased the volume of blood extracted.

Example 5

This example illustrates the effect the area of the extraction site has on the volume of blood collected.

Each of four people had his forearm (dorsal forearm, middle of forearm) punctured at 32 different positions on the forearm with a "BD ULTRA-FINE" lancet in a modified "MEDISENSE" lancet assembly. The "MEDISENSE" lancet assembly had been modified with a more powerful spring and a port had been added.

Vacuum was applied for less than five seconds prior to puncturing. The forearm was punctured under a vacuum of either −5.0 psig or −7.5 psig. The vacuum applied was maintained for 30 seconds after puncturing. The diameter of the pipette tip used to apply vacuum after puncturing was varied, with diameters of 4, 6, 8, and 10 mm being used. Four punctures per condition (diameter, vacuum level) were carried out per person. Accordingly, it can be seen that a total of 128 runs were carried out. Blood was collected into capillary tubes. The amount of blood collected was determined by measuring the length of blood in the tubes. The percentage of collections in which the volume of blood collected exceeded 1.0 μL was calculated. Sensation of pain was also recorded. Blood collection results are set forth in TABLE VA and VB.

TABLE VA vacuum level = −5.0 psig

| Vacuum diameter (mm) | Average volume of blood sample collected (μL) | Percent of samples having >1 μL of blood collected |
|---|---|---|
| 4 | 0.3 | 0 |
| 6 | 1.7 | 69 |
| 8 | 3.4 | 94 |
| 10 | 4.1 | 100 |

TABLE VB vacuum level = −7.5 psig

| Vacuum diameter (mm) | Average volume of blood sample collected (μL) | Percent of samples having >1 μL of blood collected |
|---|---|---|
| 4 | 0.8 | 25 |
| 6 | 3.1 | 94 |
| 8 | 3.4 | 81 |
| 10 | 6.3 | 94 |

The pain results were as follows:
 pain of 1=89%
 pain of 2=10%
 pain of 3=1%

The volume of blood collected and success rates (i.e., percent of samples having >1 μL of blood collected) were found to vary directly with the area of raised up into the device by the vacuum. A much greater volume of skin was raised up into the larger diameter pipette tip than into the smaller diameter pipette tips.

Example 6

This example illustrates that a plastic multiple point lancet can be used with heat and vacuum to collect a useful amount of blood.

Each of four people had his forearm (dorsal forearm, middle of forearm) punctured sixteen times (at sixteen different positions on the forearm) with a Greer Derma PIK® System for allergy testing (Greer Laboratories, Inc., Lenoir, N.C. 28645) modified to fit into a "MEDISENSE" lancet assembly. Pre-heating was carried out at approximately 40° C. and 45° C. for 15 and 60 seconds prior to puncturing. Four punctures were carried out per condition (temperature, time) per person. Accordingly, it can be seen that a total of 64 runs were carried out.

Heat was applied with a heating block, which comprised an aluminum block having one face covered with a "KAPTON" film heater element controlled by an "OMEGA" DP41 temperature controller using a T-type thermocouple and the opposite face in contact with the larger base of a frustum of a cone made of copper. The larger base of the frustum had a diameter of 0.50 in. The height of the frustum was 0.50 in. The smaller base of the frustum had a diameter of 0.35 in. The smaller base had a cylindrical opening having a diameter of 0.125 in. The cylindrical opening had a common axis with the frustum. The cylindrical opening reduced the heating surface of the copper frustum. Vacuum (−5.0 psig) was applied for a period of 30 seconds after puncturing. The vacuum in contact with the skin was formed by a pipette tip having a diameter of 8 mm. The pipette tip was held level with the plane of the skin. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE VI.

TABLE VI

| Temperature (°C.)/Time (seconds) | Average volume of blood sample collected (µL) | Percent of samples having >1 (µL) of blood collected |
|---|---|---|
| 40/15 | 2.4 | 31 |
| 40/60 | 2.6 | 50 |
| 45/15 | 2.3 | 56 |
| 45/60 | 5.2 | 81 |

The pain results were as follows:
pain of 1=100%
pain of 2=0%
pain of 3=0%

This example demonstrates that a blood extraction process employing a multi-point plastic lancet, pre-piercing heating, skin stretching, and post-piercing vacuum can extract at least 1 µL of blood at least 50% of the time.

Example 7

This example illustrates the effect of the size and the shape of the nosepiece upon the volume of blood extracted.

Each of 21 volunteers was tested thirty times in the dorsal forearm by a modified MediSense lancing assembly employing a "BD ULTRA-FINE" lancet (Becton-Dickinson). The MediSense lancing assembly had been modified with a port to allow a vacuum to effect suction through the lancing assembly. The nosepieces tested in this example were screwed onto the body of a MediSense lancing assembly in place of the conventional nosepiece. Vacuum (−7.5 psig) was applied for 10 seconds prior to lancing. After lancing, blood was collected for 30 seconds at −7.5 psig. The same nosepiece that was used prior to lancing was used for blood collection. The openings formed in the skin had a depth of 1.6 mm.

Figure 12:
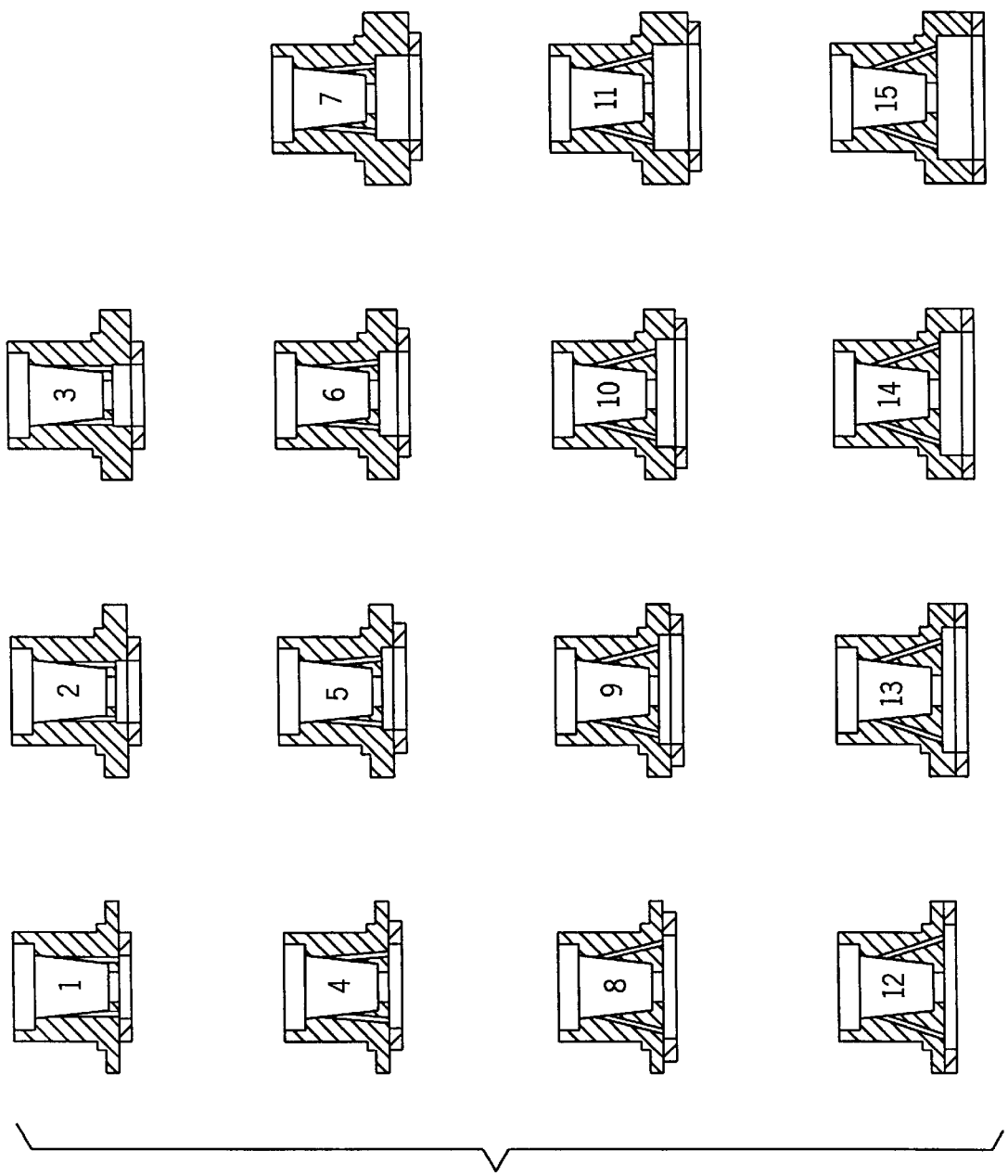
FIG. 12 is a series of elevational views of cross sections of various embodiments of nosepieces suitable for use in this invention.

Fifteen different nosepiece assemblies were evaluated. These assemblies are shown in FIG. 12. The diameter of the opening in the lower base of the nosepiece (see line "ef" in FIG. 11) varied from 9.53 to 19.05 mm. The diameter of the opening in the lower base of the nosepiece for nosepiece assemblies 1, 2, and 3 was 9.53 mm. The diameter of the opening in the lower base of the nosepiece for nosepiece assemblies 4, 5, 6, and 7 was 12.70 mm. The diameter of the opening in the lower base of the nosepiece for Nosepiece assemblies 8, 9, 10, and 11 was 15.88 mm. The diameter of the opening in the lower base of the nosepiece for nosepiece assemblies 12, 13, 14, and 15 was 19.05 mm. The rim-to-seal distances for the nosepieces (see line "bg" in FIG. 11) varied from 1.6 mm to 6.0 mm. The rim-to-seal distance for nosepieces 1, 4, 8, and 12 was 1.6 mm. The rim-to-seal distance for nosepieces 2, 5, 9, and 13 was 3.0 mm. The rim-to-seal distance for nosepieces 3, 6, 10, and 14 was 4.5 mm. The rim-to-seal distance for nosepieces 7, 11, and 15 was 6.0 mm.

The nosepieces shown in FIG. 12 had seals made from Buna N rubber. The thickness of the seals (see line "eh" in FIG. 11) was 1.6 mm and the width of the sealing surface (see line "hj" in FIG. 11) was 3.1 mm. The nosepieces had vertical walls.

Two tests were conducted per nosepiece assembly per volunteer. Blood was collected into capillary tubes. The amount of blood collected was determined by measuring the distance the blood travelled into the tube. The average amount of blood collected for each of the fifteen assemblies and the percentage of collections in which the amount of blood exceeded 1.0 µL was calculated. The results are set forth in TABLE VII.

TABLE VII

| Nosepiece number | Average volume of blood collected (µL) | Percentage having >1 µL of blood collected |
|---|---|---|
| 1 | 3.07 | 95 |
| 2 | 4.96 | 100 |
| 3 | 7.07 | 95 |
| 4 | 2.96 | 95 |
| 5 | 6.24 | 100 |
| 6 | 13.22 | 100 |
| 7 | 16.18 | 95 |
| 8 | 3.13 | 83 |
| 9 | 4.26 | 86 |
| 10 | 8.26 | 98 |
| 11 | 9.45 | 98 |
| 12 | 2.94 | 76 |
| 13 | 3.42 | 86 |
| 14 | 5.09 | 98 |
| 15 | 9.80 | 100 |

The volume blood collected and the percentage of collections exceeding 1 µL were both affected by the diameter of the opening in the lower base of the nosepiece and the rim-to-seal distance of the nosepiece. Large increases in the volume of blood collected were seen with nosepiece assemblies 6 and 7.

Example 8

This simple illustrates the effect of tapering the interior wall of the nosepiece and the time to draw blood from a person.

Glucose detectors in the form of multiple-layer elements comprising the following layers from, top to bottom, were prepared:

(1) meter-contactable layer (2) detecting layer (3) overcoat layer (4) blood-transporting layer (5) covering layer The arrangement of the layers is shown schematically in FIGS. 11A and 11B of copending application entitled METHOD AND APPARATUS FOR OBTAINING BLOOD FOR DIAGNOSTIC TESTS, Attorney's Docket No. 6005.US.P2, filed on evendate herewith, the entirety of which is incorporated herein by reference. However, the overcoat layer is substantially coplanar with the blood-transporting layer as shown in FIG. 18 of Attorney's Docket No. 6005.US.P2.

Figure 13B:
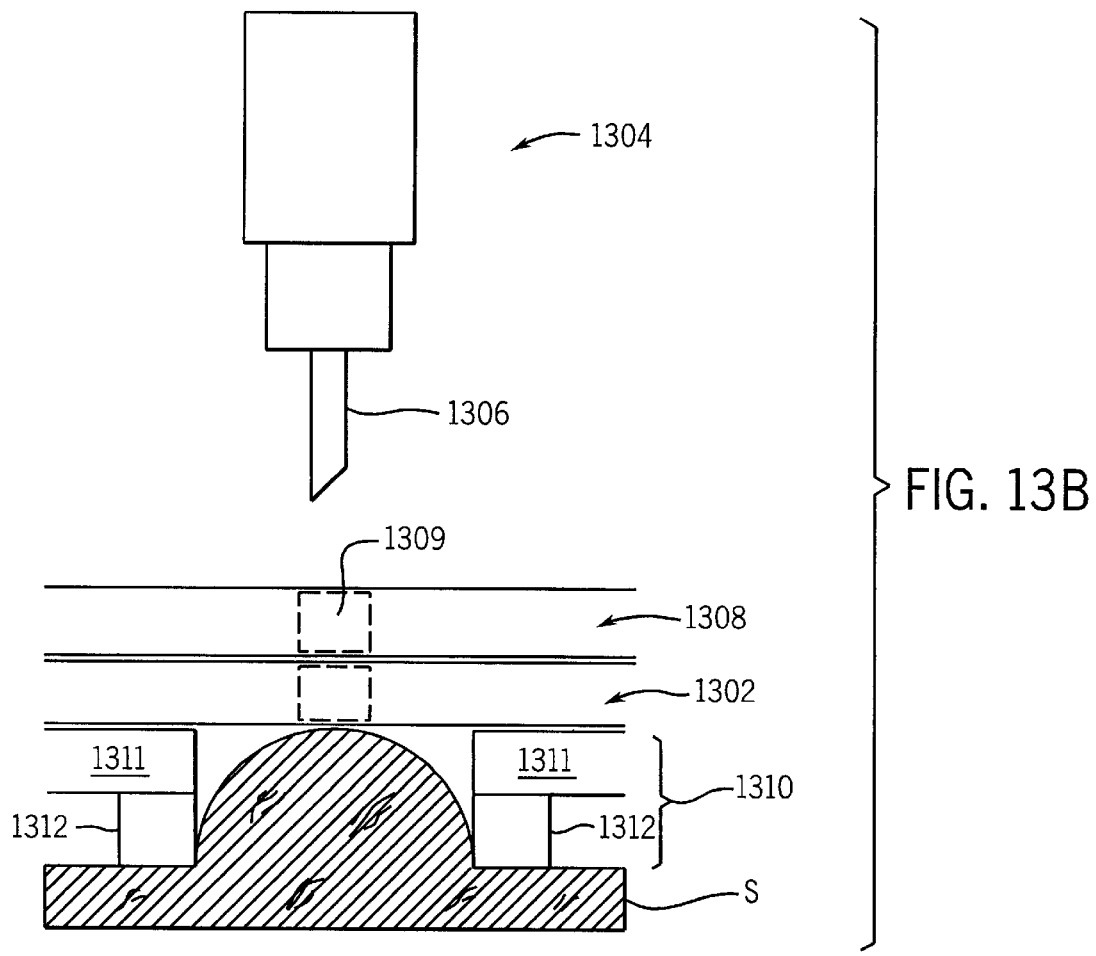
Figure 13C:
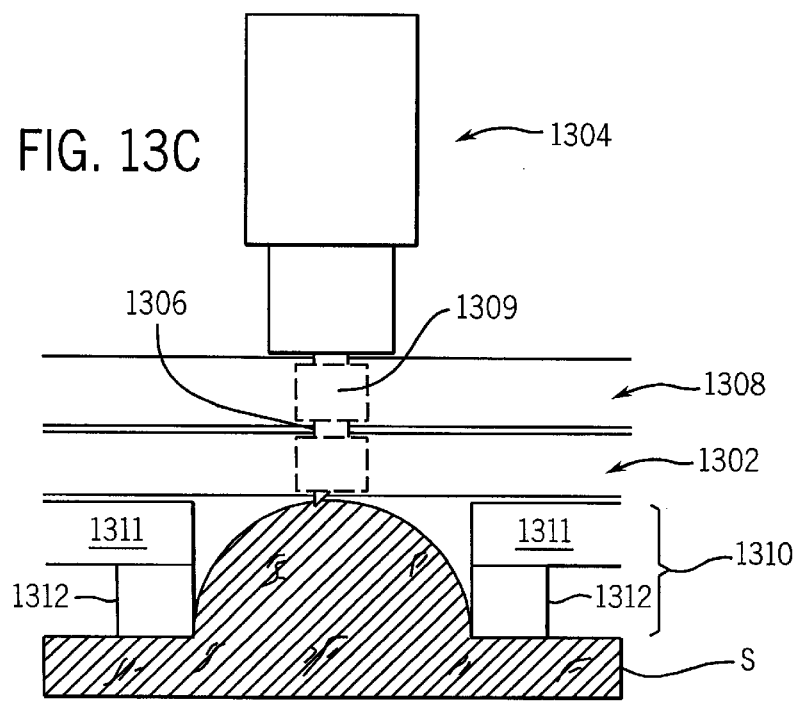
Figure 13D:
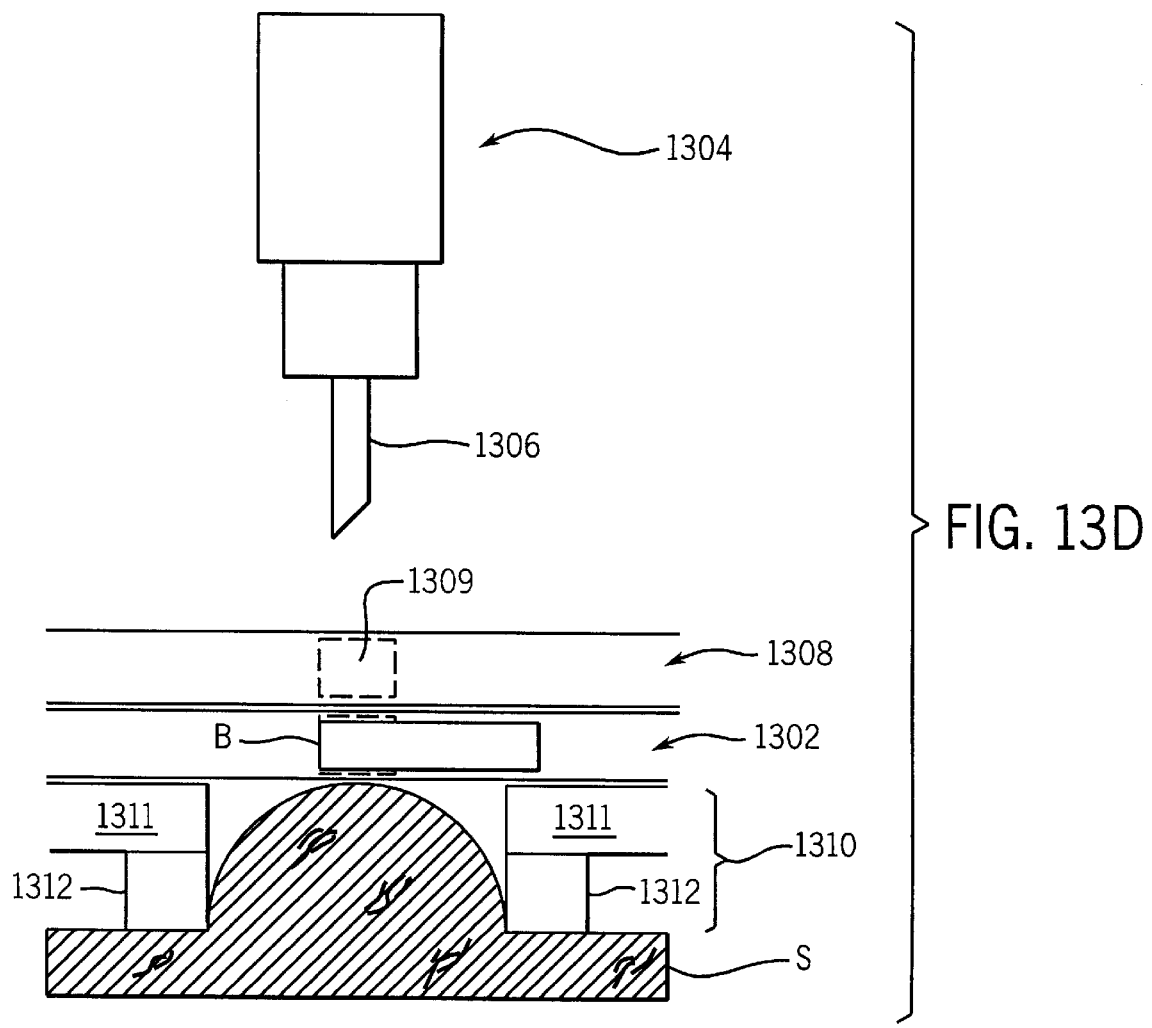
Figure 14A:
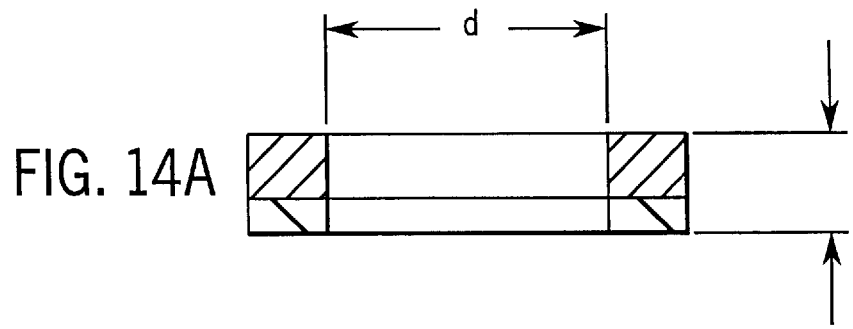
FIG. 14 is a series of elevational views of cross sections of various embodiments of nosepieces suitable for use in this invention.
Figure 14B:
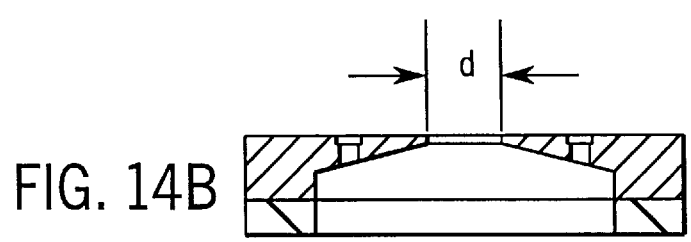
Figure 14C:
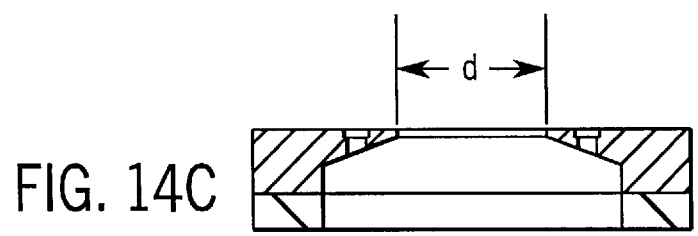
Figure 14D:
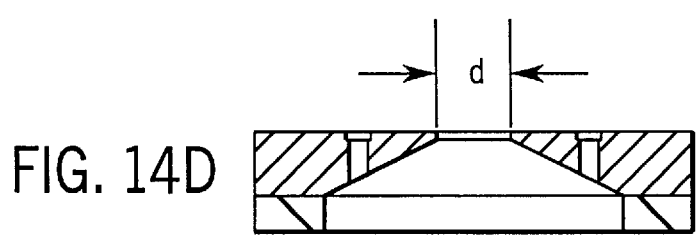
Figure 14E:
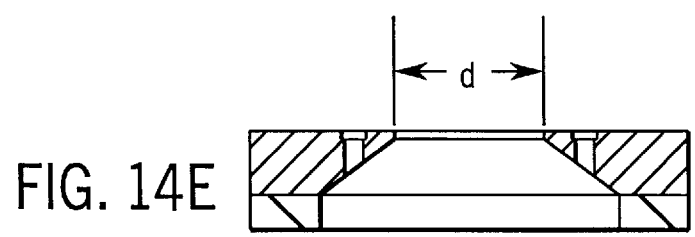

The use of a nosepiece with a detector is shown in FIGS. 13A, 13B, 13C, and 13D. The detector 1302 was placed below the lancing assembly 1304 with the openings in the detector aligned with the lancet 1306. The detector 1302 was placed between a lancet stop 1308 that contained an opening 1309 (shown in phantom) and a nosepiece assembly 1310. The nosepiece assembly included a nosepiece 1311 and a seal 1312 that contacted the skin "S". The lancing assembly 1304 prior to the application of vacuum is shown in FIG. 13A. The nosepiece assembly was placed against the forearm of a volunteer. After application of vacuum (−7.5 psig), the skin was stretched up near to or into contact with the detector as shown in FIG. 13B. The vacuum was applied for a sufficient amount of time (5 seconds) to cause the blood in the skin inside the nosepiece to pool. The lancet was then fired through the openings in the lancet stop and the detector, as shown in FIG. 13C. The lancet penetrated the skin. The lancet was then retracted as shown in FIG. 13D. The blood emerged from the opening formed in the skin, assisted by the vacuum and the stretching of the skin. The vacuum aided in the extraction of blood until the blood reached the blood-transporting layer. The blood "B" was then transported along the blood-transporting layer until it reached the detecting layer of the multiple-layer element. When the blood reached the detecting layer of the multiple-layer element, an electrical current was generated. This current was used to determine when to release the vacuum, and the skin came away from the nosepiece. The detector could then be used to analyze the blood for an analyte such as glucose.

It should be noted that the lancet stop is optional. The detector itself can be used to stop the lancet. If the detector is used to stop the lancet, the thickness of the detector is important, because it will determine the depth of penetration of the lancet.

The type of multiple-layer element used in this example had one opening in the meter-contactable layer, as shown in FIGS. 11A and 11B of Attorney's Docket No. 6005.US.P2.

Five varieties of nosepieces were used in this example. These nosepieces are shown in cross-section in FIG. 14. The nosepieces varied in the areas of the opening in the upper base, and the distance from the lower base at which tapering of the interior wall began. The diameters "d" of the openings in the upper base for each nosepiece was as follows:

| Nosepiece | Diameter of opening in upper base (mm) |
|---|---|
| A | 12.7 |
| B | 3 |
| C | 6 |
| D | 3 |
| E | 6 |

Figure 15:
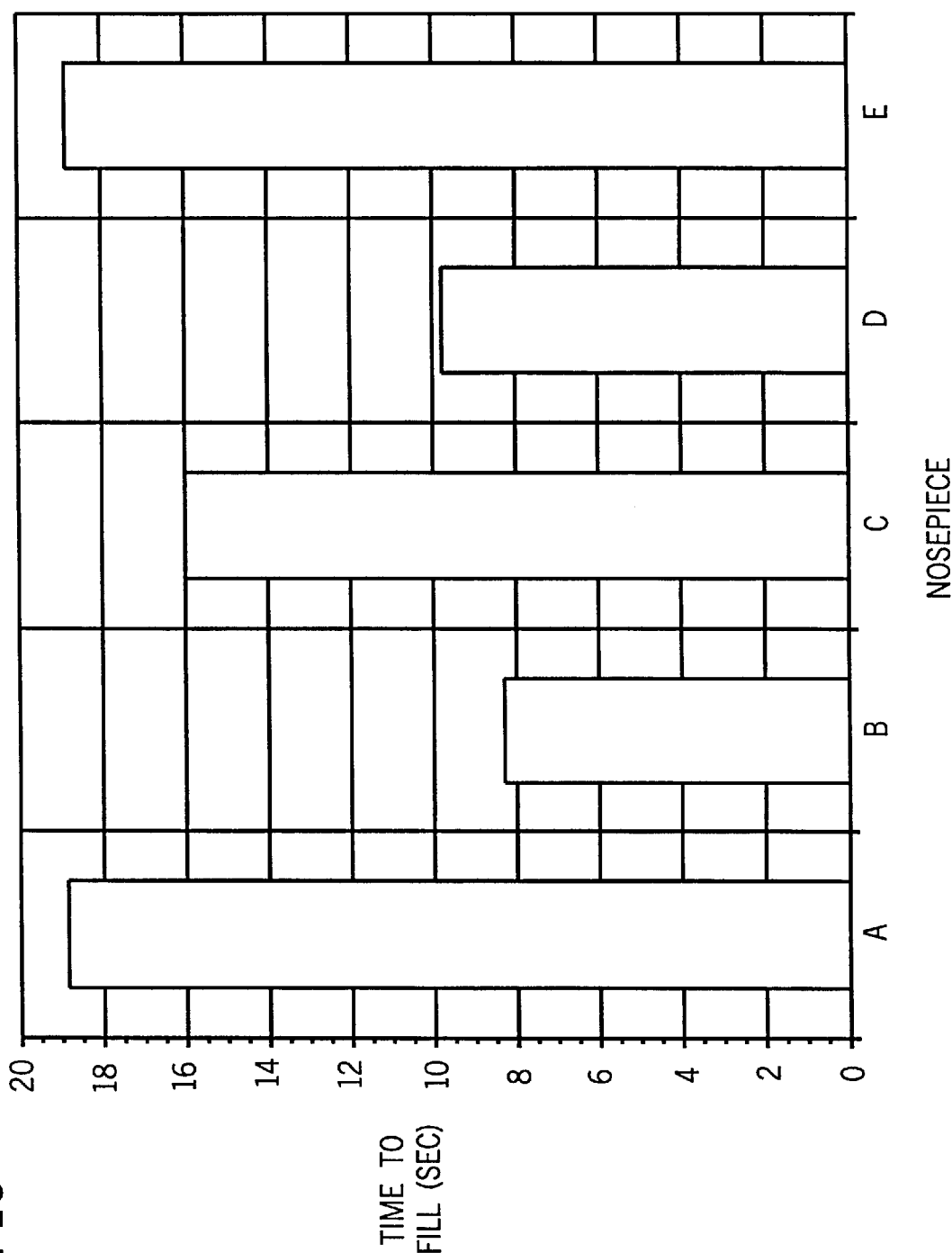
FIG. 15 is a graph illustrating the effect that various embodiments of nosepieces have on filling time of a detecting element.

The rim-to-seal distance (see line "bg" in FIG. 11), 4.5 mm, and the diameter of the opening in the lower base of the nosepiece (see line "ef" in FIG. 11), 12.7 mm, was the same for all five nosepieces. The nosepiece assemblies shown in FIG. 14 had seals made from Buna N rubber, 40A durometer hardness. The thickness of the seals (see line "eh" in FIG. 11) was 1.6 mm, and the width of the sealing surface (see line "hj" in FIG. 11) was 3.1 mm Eight volunteers were tested as described above. Each volunteer was tested 10 times with nosepiece A and four times with each of the remaining nosepieces, B, C, D, and E in FIG. 14. The time required for the multiple-layer element to fill was recorded. The element was considered filled when a current of 1.5 microamperes ($\mu A$) was generated by the element. The vacuum was then released. The average time required to reach 1.5 $\mu A$ for each nosepiece was calculated and is shown in FIG. 15. The smaller the diameter of the opening in the upper base, the less time was required to fill the detector.

Example 9

This example illustrates the effect of tapering the interior wall of the nosepiece upon the time to draw blood and the success of drawing blood from a volunteer from whom drawing blood was typically difficult.

Figure 16:
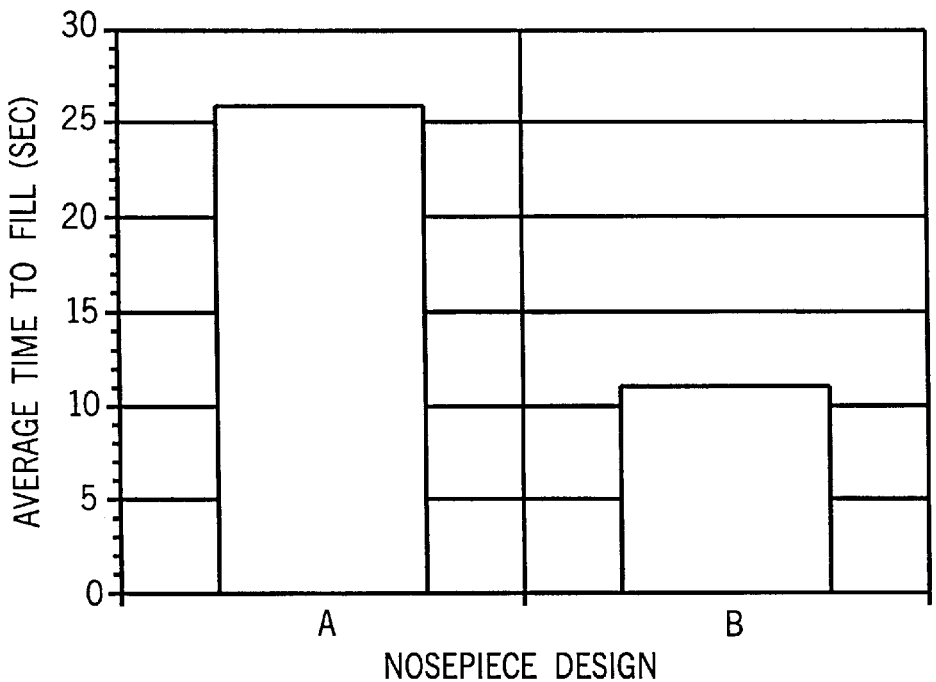
FIG. 16 is a graph illustrating the average time to fill a multiple-layer element as a function of the nosepiece used.
Figure 17:
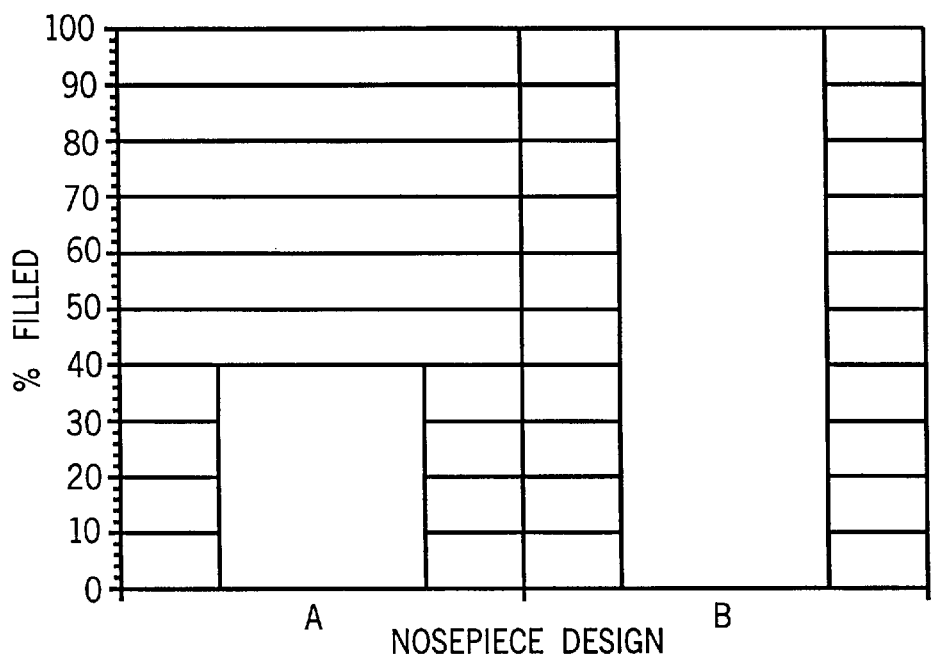
FIG. 17 is a graph illustrating the percent filled, as a function of the nosepiece used.
Figure 18A:
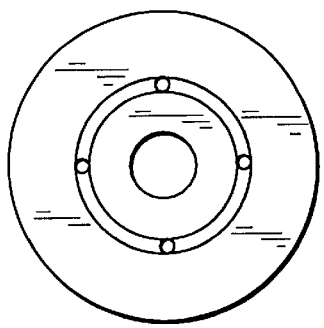
FIG. 18 is a series of elevational views of cross sections and top plan views of various embodiments of nosepieces suitable for use in this invention
Figure 18F:
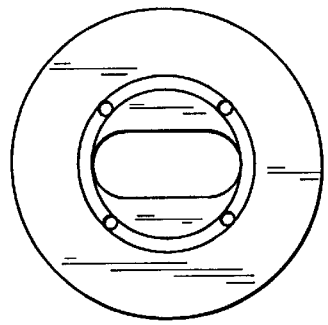
Figure 18B:
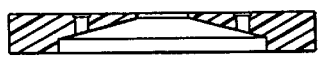
Figure 18C:
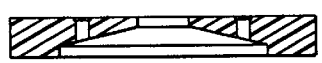
Figure 18G:
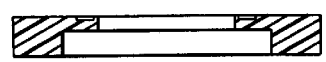
Figure 18D:
Figure 18H:
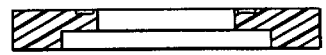
Figure 18E:
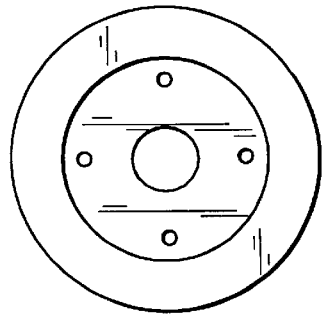
Figure 18I:
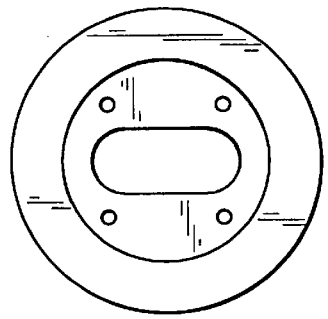

The experiment was conducted as described in Example 8 with the following exceptions. Only nosepieces having the configurations of nosepieces A and B were used in the example. The diameter of the opening in the upper base on nosepiece B was four millimeters instead of the three millimeter opening used in Example 8. The volunteer was tested 10 times using nosepiece A. The volunteer was also tested 10 times with nosepiece B. The average time required to fill the multiple-layer element was calculated for elements that filled in 40 seconds or less and is shown in FIG. 16. The percentage of multiple-layer elements that filled in 40 seconds or less was calculated and is shown in FIG. 17.

The nosepiece having the opening in the upper base having a diameter of less than the diameter of the opening in the lower base, nosepiece 13, filled in less than half the time required by a nosepiece where the diameter of the opening in the upper base was equal to the diameter of the opening in the lower base, nosepiece A. The percentage of multiple-layer elements that were filled in under 40 seconds was significantly improved for nosepiece B, as compared with nosepiece A.

Example 10

This example illustrates the effect of the shape of the opening in the upper base upon the time required to draw blood from a person.

Glucose detectors in the form of multiple-layer elements comprising the following layers, from top to bottom, were prepared:

(1) meter-contactable layer (2) detecting layer
(3) overcoat layer
(4) blood-transporting layer
(5) covering layer The arrangement of the layers is shown schematically in FIGS. 11A and 11B of copending application entitled METHOD AND APPARATUS FOR OBTAINING BLOOD FOR DIAGNOSTIC TESTS, Attorney's Docket No. 6005.US.P2, filed on evendate herewith, the entirety of which is incorporated herein by reference. However, the overcoat layer is substantially coplanar with the blood-transporting layer as shown in FIG. 18 of Attorney's Docket No. 6005.US.P2.

The use of a nosepiece with a detector is shown in FIGS. 13A, 13B, 13C, and 13D. The detector 1302 was placed below the lancing assembly 1304 with the openings in the detector aligned with the lancet 1306. The detector 1302 was placed between a lancet stop 1308 that contained an opening 1309 (shown in phantom) and a nosepiece assembly 1310. The nosepiece assembly 1310 included a nosepiece 1311 and a seal 1312 that contacted the skin "S". The lancing assembly 1304 prior to the application of vacuum is shown in FIG. 13A. The nosepiece assembly 1304 was placed against the forearm of a volunteer. After application of vacuum (−7.5 psig), the skin was stretched up near to or into contact with the detector as shown in FIG. 13B. The vacuum was applied for a sufficient amount of time (5 seconds) to cause the blood in the skin inside the nosepiece to pool. The lancet was then fired through the openings in the lancet stop and the detector, as shown in FIG. 13C. The lancet penetrated the skin. The lancet was then retracted, as shown in FIG. 13D. The blood emerged from the opening formed in the skin, assisted by the vacuum and the stretching of the skin. As quickly as possible, the multiple-layer element was slid approximately 2 mm in the direction away from the electrical contacts. This type of movement is more fully described in copending application entitled METHOD AND APPARATUS FOR OBTAINING BLOOD FOR DIAGNOSTIC TESTS, Attorney's Docket No. 6005.US.P4, filed on evendate herewith, the entirety of which is incorporated herein by reference. The vacuum aided in the extraction of blood until the blood reached the blood-transporting layer. The blood "B" was then transported along the blood-transporting layer until it reached the detecting layer of the multiple-layer element. When the blood reached the detecting layer of the multiple-layer element, an electrical current was generated. This current was used to determine when to release the vacuum, and the skin came away from the nosepiece. The detector could then be used to analyze the blood for an analyte such as glucose.

It should be noted that the lancet stop is optional. The detector can be used to stop the lancet. If the detector is used to stop the lancet, the thickness of the detector is important, because it will determine the depth of penetration of the lancet.

The type of multiple-layer element used in this example had two openings in the meter-contactable layer, as shown in FIG. 16A of Attorney's Docket No. 6005.US.P2.

A pneumatic lancing assembly was used to fire the lancet. The pneumatic lancing assembly was the type of lancing assembly described in FIGS. 16 and 17 of copending application entitled METHOD AND APPARATUS FOR OBTAINING BLOOD FOR DIAGNOSTIC TESTS, Attorney's Docket No. 6005.US.P1, filed on evendate herewith, the entirety of which is incorporated herein by reference.

Five variations of nosepiece assemblies were used in this example. They are shown in top view and cross section in FIG. 18. The nosepieces varied in the depth of the rim (see line "ab" in FIG. 11) and the shape of the opening in the upper base. The rim-to-seal distance plus the depth of the rim, 4.0 mm, (see line "bg" plus line "ab" in FIG. 11) and the diameter of the opening in the lower base of the nosepiece, 12.7 mm, (see line "ef" in FIG. 11) was the same for all five nosepieces.

Eight volunteers were tested on the dorsal forearm as described above. Each volunteer was tested four times with each of the five nosepieces, for a total of 20 tests per volunteer. The time for the detector to fill after lancing was recorded. The detector was considered filled when a current of 1.5 $\mu$A was generated. The vacuum was then released. The average time required to reach a current of 1.5 $\mu$A for the five nosepieces was calculated and is shown in TABLE VIII.

TABLE VIII

| Nosepiece | Depth of rim (mm) | Shape of opening in upper base | Average time to reach 1.5 $\mu$A (sec) |
|---|---|---|---|
| A | 0.38 | Circle | 7.6 |
| B | 0.76 | Circle | 11.6 |
| C | 0.76 | Circle | 13.5 |
| D | 0.76 | Oval | 8.6 |
| E | 1.3 | Oval | 12.6 |

The nosepieces as shown in FIG. 18 had seals made from Buna N rubber, 40A durometer. The thickness of the seal (see line "eh" in FIG. 11) was 1.6 mm and the width of the sealing surface (see line "hj" in FIG. 11) was 3.1 mm.

For a given opening shape, the nosepieces having rims of lower depth required less time to fill the detector than did those nosepieces having rims of greater depth. For a given depth of rim, the nosepieces having oval rim openings required less time to fill the detector than did nosepieces having circular rim openings.

Example 11

This example illustrates the effect of different sealing materials upon the ability to form a good vacuum seal to a hairy arm.

Seals were punched out from sheets of different sealing materials. The eight materials used are listed in TABLE IX. The seals, which were circular in shape, had a sealing surface width (see line "hj" in FIG. 11) of 3.1 mm. Each seal was then utilized in a nosepiece, as shown in FIG. 11. The seals were attached to the lower base of the nosepiece by means of an adhesive. The distance from the rim to the lower base of nosepiece prior to attachment of the seal was 1.5 mm. After the attachment of the seal, the rim-to-seal distance of the nosepiece was variable due to the differences in the thickness of the seal.

Figure 19:
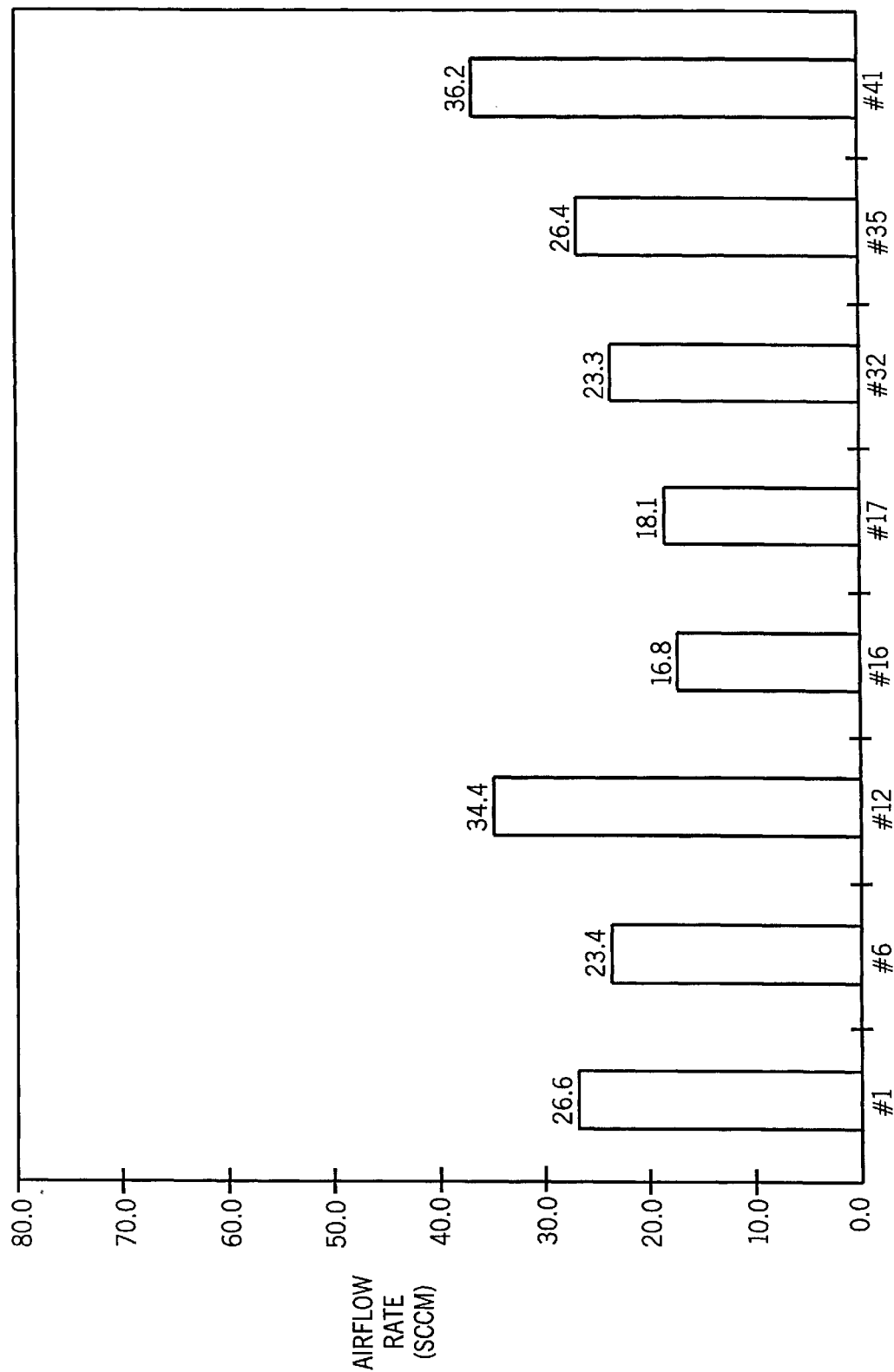
FIG. 19 is a graph illustrating airflow rate as a function of the nosepiece used.

A vacuum port was attached to the nosepiece to allow a vacuum source to effect suction through the nosepiece. An air flow meter (Alicat Scientific, Tucson, Ariz., Model #PVM200SCCM-D-S-A) was attached between the vacuum source and the nosepiece. The nosepiece was attached to a holder. The combined weight of the nosepiece and holder was 230 grams. A male volunteer who had more hair on his dorsal forearm than did the average male population was chosen. The volunteer placed his arm against the seal of the nosepiece so as to bring the full weight of the nosepiece and holder against the arm. The purpose of this apparatus was to provide a constant pressure. A vacuum of −8 psig was applied. The ability of the seal to seal to the skin was measured by the amount of air leaking into the nosepiece, as measured by the air flow meter in the units of standard cubic centimeters per minute (SCCM). The measurement was repeated at a total of 20 locations on the volunteer's forearm for each of the seal types. The average leakage rate at the twenty forearm sites for each of the seal materials is shown in FIG. 19.

All the materials were capable of limiting the average leakage rate to below 40 SCCM on the volunteer. The leakage rate is important because the size of the vacuum pump required is directly proportional to the leakage rate. In addition, a low leakage rate will result in improved battery life. A small vacuum pump can be used at a low leakage rate. The low leakage rates obtained allow a commercially available miniature vacuum pump, such as that available from T-Squared Manufacturing Company, Nutley, N.J., and having the part number T2-03.08.004, to be used with the apparatus. The low leakage rates obtained with the seal materials tested mean that cumbersome methods of attaching the nosepiece to the skin to achieve a good seal are not needed. Other methods to attach the nosepiece to the skin to form a vacuum seal are not preferred. An adhesive is not preferred because it will make the nosepiece assembly difficult to remove, and it can cause pain to the user when the seal is removed. Grease is not preferred because it will leave a residue after the test is complete.

TABLE IX

| Seal no. | Material | Manufacturer/Supplier | Thickness (mm) |
|---|---|---|---|
| 1 | silicone rubber, 50A durometer | McMaster Carr, #8632K921 | 1.6 |
| 6 | neoprene/SBR/EPDM blend foam | Jessup Mfg. | 3.2 |
| 12 | silicone rubber | unknown | 1.6 |
| 16 | neoprene, 5-10A durometer | McMaster Carr, #8639K512 | 1.6 |
| 17 | Buna-N rubber, 40A durometer | McMaster Carr, #86715K102 | 1.6 |
| 32 | chlorinated polyisoprene | Ashland Rubber, #90-5271 | 1.9 |
| 35 | neoprene | Pres-On Corp., #p-8100 | 3.2 |
| 41 | rubber | Standard Rubber Company, #4119N/SCE-41 | 1.6 |

Example 12

This example illustrates the effect of different sealing materials upon the amount of blood extracted from a person.

Figure 20:
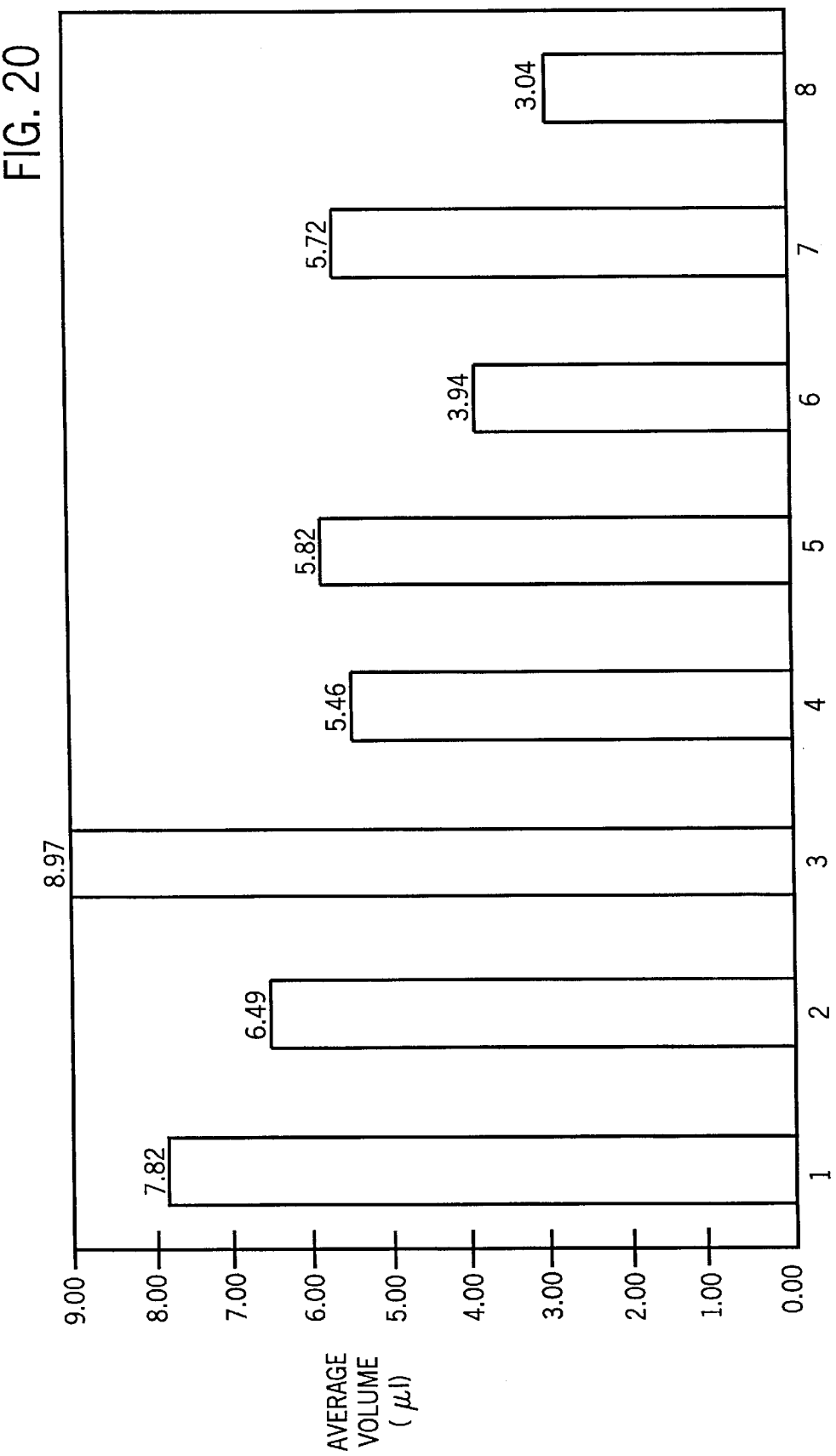
FIG. 20 is a graph illustrating the average volume of blood collected as a function of the material used to make the seal of the nosepiece assembly.

Each of four volunteers was tested 32 times in the dorsal forearm by a modified MediSense lancing assembly employing a "BD ULTRA-FINE" lancet. The MediSense lancing assembly had been modified with a port to allow a vacuum to effect suction through the lancing assembly. The nosepieces tested in this example were screwed onto the body of a MediSense lancing assembly in place of the conventional nosepiece. Vacuum (−7.5 psig) was applied for five seconds prior to lancing. Blood was collected after lancing for 30 seconds at −7.5 psig using the same nosepiece as was used prior to lancing. The depth setting of the lancet was 1.6 mm. Eight different nosepiece assemblies were evaluated Four tests were conducted per nosepiece assembly per volunteer. Blood was collected into capillary tubes. The amount of blood collected was determined by measuring the length of blood in the tube. The average amount of blood collected for each of the eight nosepiece assemblies is shown in FIG. 20.

For the eight different nosepiece assemblies, the diameter of the opening in the base (see line "ef" in FIG. 11) was 10 mm, the diameter of the opening in the upper base (see line "cd" in FIG. 11) was 4 mm, the rim-to-seal distance (see line "bg" in FIG. 11) was 3 mm, and the width of the sealing surface (see line "hj" in FIG. 11) was 3.1 mm. The nosepiece assemblies differed in the material used for the nosepiece seal and the thickness of the seal. The eight variations of sealing material and thicknesses thereof are listed in TABLE X.

TABLE X

| Nosepiece no. | Sealing material | Manufacturer/Supplier | Thickness (mm) |
|---|---|---|---|
| 1 | Buna N, 40A durometer | McMaster Carr, #86715K102 | 1.6 |
| 2 | Buna N, 40A durometer | McMaster Carr, #86715K102 | 3.2 |
| 3 | Buna N, 60A durometer | McMaster Carr, #86305K421 | 1.6 |
| 4 | sorbothane | Sorbothane Inc. | 1.6 |
| 5 | sorbothane, siliconized | Sorobothane Inc., siliconized by Applied Membrane Technology | 1.6 |
| 6 | neoprene, 5–10A durometer | McMaster Carr, #8639K512 | 1.6 |
| 7 | closed cell toam | UFP Technology, #G-231N | 1.6 |
| 8 | neoprene/SBR/EPDM blend foam | Jessup | 3.2 |

All of the eight different nosepiece seal materials sealed well enough to the skin to enable the extraction of on average greater than 3 $\mu$L of blood in 30 seconds. The hardest material of the eight tested, Buna N-60A durometer, had the highest blood extraction rate. Increasing the seal thickness from 1.6 to 3.2 mm had little effect on the volume of blood collected in 30 seconds.

Example 13

This example illustrates the effect of using a novel seal upon the time required to extract blood from a person.

Glucose detectors in the form of multiple-layer elements comprising the following layers, from top to bottom, were prepared:

(1) meter-contactable layer (2) detecting layer (3) overcoat layer (4) blood-transporting layer (5) covering layer The arrangement of the layers is shown schematically in FIGS. 11A and 11B of copending application entitled METHOD AND APPARATUS FOR OBTAINING BLOOD FOR DIAGNOSTIC TESTS, Attorney's Docket No. 6005.US;.P2, filed on evendate herewith, the entirety of which is incorporated herein by reference. However, the overcoat layer is substantially coplanar with the blood-transporting layer as shown in FIG. 18 of Attorney's Docket No. 6005.US.P2.

The use of a nosepiece with a detector is shown in FIGS. 13A, 13B, 13C, and 13D. The detector 1302 was placed below the lancing assembly 1304 with the openings in the detector aligned with the lancet 1306. The detector 1302 was placed between a lancet stop 1308 that contained an opening 1309 (shown in phantom) and a nosepiece assembly 1310. The nosepiece assembly 1310 included a nosepiece 1311 and a seal 1312 that contacted the skin "S". The lancing assembly 1304 prior to the application of vacuum is shown in FIG. 13A. The nosepiece assembly was placed against the forearm of a volunteer. After application of vacuum (−7.5 psig), the skin was stretched up near to or into contact with the detector as shown in FIG. 13B. The vacuum was applied for a sufficient amount of time (5 seconds) to cause the blood in the skin inside the nosepiece to pool. The lancet was then fired through the openings in the lancet stop and the detector, as shown in FIG. 13C. The lancet penetrated the skin. The lancet was then retracted, as shown in FIG. 13D. The blood emerged from the opening formed in the skin, assisted by the vacuum and the stretching of the skin. The vacuum aided in the extraction of blood until the blood reached the blood-transporting layer. The blood "B" was then transported along the blood-transporting layer until it reached the detecting layer of the multiple-layer element. When the blood reached the detecting layer of the multiple-layer element, an electrical current was generated. This current was used to determine when to release the vacuum, and the skin came away from the nosepiece. The detector could then be used to analyze the blood for an analyte such as glucose.

It should be noted that the lancet stop is optional. The detector itself can be used to stop the lancet. If the detector is used to stop the lancet, the thickness of the detector is important, because it will determine the depth of penetration of the lancet.

A pneumatic lancing assembly was used to fire the lancet. The pneumatic lancing assembly was the type of lancing assembly described in FIGS. 11, 12, 13, and 14 of copending application entitled METHOD AND APPARATUS FOR OBTAINING BLOOD FOR DIAGNOSTIC TESTS of Attorney's Docket No. 6005.US.P1, filed on evendate herewith, the entirety of which is incorporated herein by reference.

The type of multiple-layer element used in this example had one opening in the meter-contactable layer, as shown in FIGS. 11A and 11B of Attorney's Docket No. 6005.US.P2.

Two nosepiece assembly variations were used in this example. The size and structure of both nosepieces in the nosepiece assemblies were the same as that of nosepiece B of FIG. 14, with the exception that the diameter of the opening in the upper base was increased to 4 mm. One nosepiece had a planar Buna N seal, 40 durometer (see FIG. 11). The other nosepiece had a seal of the type shown in FIGS. 21A and 21B in cross section, referred to hereinafter as a flex seal. The flex seal contacts a larger area of skin than does a planar seal. The flex seal can then cause more skin to be brought into the internal space of the nosepiece when vacuum is applied than can a planar seal. The flex seal was made out of a silicone, 40A durometer.

Figure 21A:
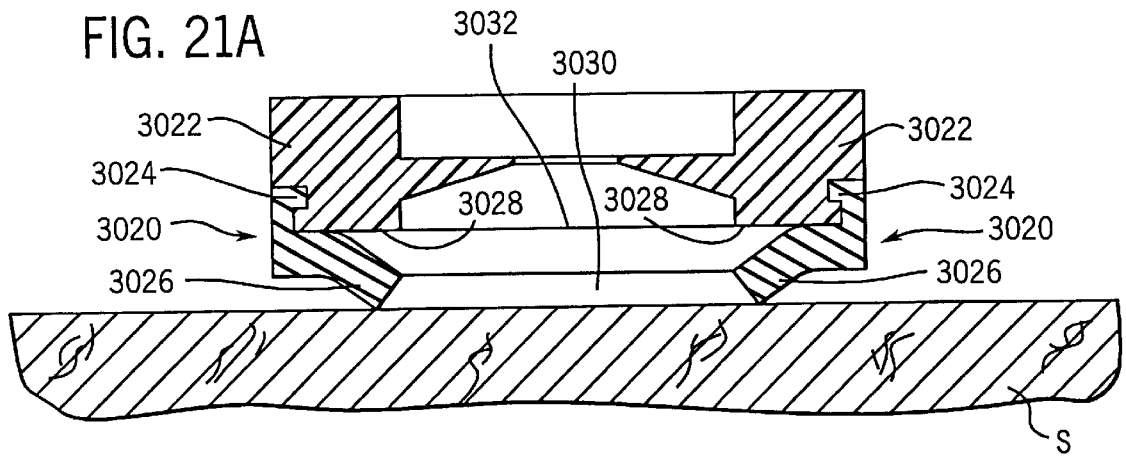
FIG. 21A is an elevational view of a cross section of a preferred embodiment of a nosepiece of this invention, wherein the seal is in a first position.
Figure 21B:
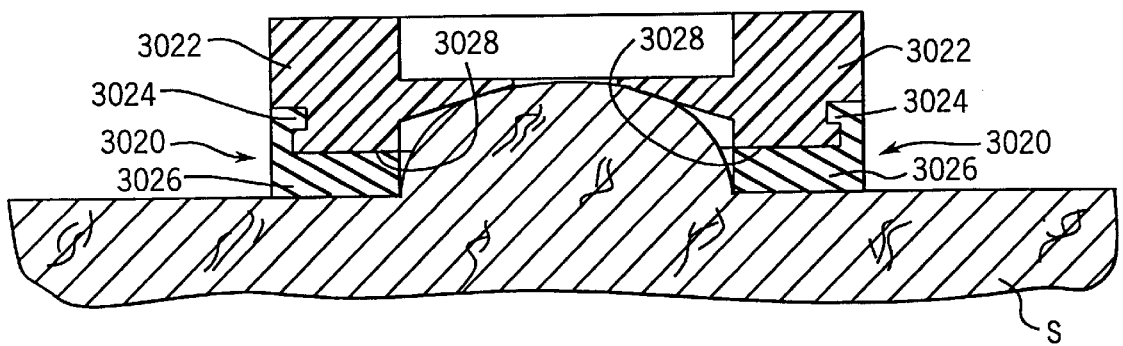
FIG. 21B is an elevational view of the nosepiece of FIG. 21A, wherein the seal is in a second position.

The flex seal 3020 can be attached to the nosepiece 3022 by a mechanical attachment 3024 or by an adhesive. The portion 3026 of the flex seal that is not attached to the nosepiece 3022 is capable of moving between a first position, as shown in FIG. 21A, and a second position, as shown in FIG. 21B. In the first position, the unattached portion 3026 of the flex seal 3020 depends from the lower base 3028 of the nosepiece 3022 as shown in FIGS. 21A. In the second position, the unattached portion 3026 of the flex seal 3020 contacts the lower base 3028 of the nosepiece 3022 such that one major surface of the unattached portion of the seal is in face-to-face contact with the lower base 3028 of the nosepiece as shown in FIG. 21B. The flex seal is made of a material having a coefficient of friction that reduces the tendency of skin in contact with it to slide. The seal should be sufficiently flexible so that it can move between the first position and the second position and sufficiently stiff to hold the skin in an immovable position. The opening 3030 in the flex seal has an area greater than the area of the opening 3032 in the lower base 3028 of the nosepiece 3022, when the flex seal is in the first position, as shown in FIG. 21A.

In operation, the flex seal, is placed against the skin "S" of the patient. The area of skin contacted by the flex seal is greater than the area of the opening in the lower base of the nosepiece. Consequently, the volume of skin lifted into the nosepiece is greater than the volume of skin that would have been lifted into the nosepiece with a planar seal. Thus, the flex seal would be beneficial for a patient having below normal skin flexibility.

Eight volunteers were tested on the dorsal forearm substantially in the manner described previously. In the previous examples, the nosepiece assembly was manipulated by moving it from side to side or toward and away from the skin. In this example, the nosepiece assembly was not moved after it was placed against the skin. Each volunteer was tested eight times using the planar seal and flex seal configurations for a total of 16 tests per volunteer. The time to fill the detector after lancing was recorded. The detector was considered filled when a current of 1.5 $\mu$A was generated. The vacuum was then released. The average time required for the current to reach 1.5 $\mu$A for the flex seal was 14.9 seconds and the average time required for the current to reach 1.5 $\mu$A for the planar seal was 17.9 seconds.

The nosepiece employing the flex seal required less time to fill the detector than did the nosepiece employing a planar seal. Moreover, manipulation of the nosepiece assembly was eliminated.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A nosepiece suitable for use with a vacuum aided blood vacuum aided collection apparatus, said nosepiece comprising:
    (a) a lower base having an opening therein;
    (b) an upper base having an opening therein;
    (c) an interior wall joining said upper base and said lower base, the area of said opening in said upper base being less than the area of said opening in said lower base; and
    (d) a seal attached to said lower base of said nosepiece, the distance between the lowermost point of said seal and the lowermost point of said upper base be such that skin, when stretched into said nosepiece, comes as close as possible to said upper base or contacts said upper base.

2. The nosepiece of claim 1, further including at least one passageway for vacuum.

3. The nosepiece of claim 1, wherein said opening in said upper base is circular in shape.

4. The nosepiece of claim 1, wherein said opening in said upper base is oval in shape.

5. The nosepiece of claim 1, wherein said interior wall is tapered.

6. The nosepiece of claim 1, wherein said interior wall is comprised of stepwise cylindrical sections.

7. A nosepiece suitable for use with a vacuum aided blood collection apparatus, said nosepiece comprising:
    (a) a lower base having an opening therein;
    (b) an upper base having an opening therein;
    (c) an interior wall joining said upper base and said lower base, the area of said opening in said upper base being less than the area of said opening in said lower base, wherein said opening in said upper base is surrounded by a rim; and
    (d) a seal attached to said lower base of said nosepiece, the distance between the lowermost point of said seal and the lowermost point of said rim be such that skin, when stretched into said nosepiece, comes as close as possible to said rim or contacts said rim.

8. The nosepiece of claim 1, further including a seal attached to said lower base of said nosepiece.

9. The nosepiece of claim 8, wherein said seal is in the form of an annular ring.

10. A nosepiece suitable for use with a vacuum aided blood collection apparatus, said nosepiece comprising:

(a) a lower base having an opening therein;

(b) an upper base having an opening therein; and (c) an interior wall joining said upper base and said lower base, the area of said opening in said upper base being less than the area of said opening in said lower base, further including a seal attached to said lower base of said nosepiece, wherein said seal is capable of moving between a first position and a second position.

11. The nosepiece of claim 8, wherein said seal is formed from rubber or an elastomeric material.

12. The nosepiece of claim 8, wherein said seal is formed from an adhesive.

13. The nosepiece of claim 1, wherein the ratio of the diameter of the opening in the lower base to the diameter of the opening in the upper base is at least about 3 to 1.

14. The nosepiece of claim 1, wherein the distance between the lowermost point of said seal and the lowermost point of said upper base ranges from about 1.5 mm to about 8.0 mm.

15. The nosepiece of claim 7, further including at least one passageway for vacuum.

16. The nosepiece of claim 7, wherein said opening in said upper base is circular in shape.

17. The nosepiece of claim 7, wherein said opening in said upper base is oval in shape.

18. The nosepiece of claim 7, wherein said interior wall is tapered.

19. The nosepiece of claim 7, wherein said interior wall is comprised of stepwise cylindrical sections.

20. The nosepiece of claim 7, wherein said seal is in the form of an annular ring.

21. The nosepiece of claim 7, wherein said seal is formed from rubber or an elastomeric material.

22. The nosepiece of claim 7, wherein said seal is formed from an adhesive.

23. The nosepiece of claim 7, wherein the ratio of the diameter of the opening in the lower base to the diameter of the opening in the upper base is at least about 3 to 1.

24. The nosepiece of claim 7, wherein the distance between the lowermost point of said seal and the lowermost point of said rim ranges from about 1.5 mm to about 8.0 mm.

25. The nosepiece of claim 10, further including at least one passageway for vacuum.

26. The nosepiece of claim 10, wherein said opening in said upper base is circular in shape.

27. The nosepiece of claim 10, wherein said opening in said upper base is oval in shape.

28. The nosepiece of claim 10, wherein said interior wall is tapered.

29. The nosepiece of claim 10, wherein said interior wall is comprised of stepwise cylindrical sections.

30. The nosepiece of claim 10, wherein said seal is formed from rubber or an elastomeric material.

31. The nosepiece of claim 10, wherein said seal is formed from an adhesive.

32. The nosepiece of claim 10, wherein the ratio of the diameter of the opening in the lower base to the diameter of the opening in the upper base is at least about 3 to 1.

* * * * *